United States Patent [19]
Benowitz et al.

[11] Patent Number: 5,898,066
[45] Date of Patent: Apr. 27, 1999

[54] TROPHIC FACTORS FOR CENTRAL NERVOUS SYSTEM REGENERATION

[75] Inventors: Larry I. Benowitz; Carleen A. Irwin, both of Newton; Paul Jackson, Brookline, all of Mass.

[73] Assignee: Children's Medical Center Corporation, Boston, Mass.

[21] Appl. No.: 08/296,661

[22] Filed: Aug. 26, 1994

[51] Int. Cl.$^6$ ............................ C07K 2/00; C07K 14/475
[52] U.S. Cl. ............................................ 530/300; 530/399
[58] Field of Search .................................. 530/300, 350, 530/399; 514/2, 12

[56] References Cited

U.S. PATENT DOCUMENTS

| | | | |
|---|---|---|---|
| 3,625,214 | 12/1971 | Higuchi | 128/260 |
| 4,244,946 | 1/1981 | Rivier et al. | 424/177 |
| 4,305,872 | 12/1981 | Johnston et al. | 260/112.5 R |
| 4,316,891 | 2/1982 | Guillemin et al. | 424/177 |
| 4,629,784 | 12/1986 | Stammer | 530/328 |
| 4,789,734 | 12/1988 | Pierschbacher | 530/395 |
| 4,792,525 | 12/1988 | Ruoslahti et al. | 435/240.243 |
| 4,868,116 | 9/1989 | Morgan et al. | 435/240.2 |
| 4,906,474 | 3/1990 | Langer et al. | 424/428 |
| 4,925,673 | 5/1990 | Steiner et al. | 424/455 |
| 4,980,286 | 12/1990 | Morgan et al. | 435/172.3 |

FOREIGN PATENT DOCUMENTS

WO 93/01286  1/1993  WIPO.

OTHER PUBLICATIONS

Aguayo, A.J., et al., "Degeneration and regeneration of injured neurons in the nervous system of adult mammals," *Phil. Trans. Royal Soc. London, Series B*, 331:337–343 (1991).

Altschuler, D., et al., "Taurine promotes the differentiation of a vertebrate retinal cell type in vitro," *Development*, 119:1317–1328 (1993).

Barde, Y.A., et al., "Purification of a new neutrophic factor from mammalian brain," *EMBO. J.* 1:549–553 (1982).

Burrell, H.R., et al., "RNA metabolism in the goldfish retina during optic nerve regeneration," *J. Neurochem.*, 31:289–298 (1978).

Caroni, P. and M.E., Schwab, "Two membrane protein fractions from rat central myelin with inhibitory properties for neurite growth and fibroblast spreading," *J. Cell Biol.*, 106:1281–1288 (1988).

Crooke, Stanley T., "Progress toward oligonucleotide therapeutics: pharmacodynamic properties," *FASEB J.* 7, 533–539 (1993).

Ford-Holevinski, T.S., et al., "Laminin supports neurite outgrowth from the explants of axotomized adult retinal neurons," *Brain Research* 28:121–126 (1986).

Ghosh, A., et al., "Requirement for BDNF in activity-dependent survival of cortical neurons," *Science* 263:1618–1623 (1994).

Hall, C.M., et al., "Neuronal intermediate filament expression during neurite outgrowth from explanted goldfish retina: effect of retinoic acid," *J. Neurochem.* 55:1671–82 (1990).

Inai, T., et al., "Immunohistochemical detection of an enamel protein–related epitope in rat bone at an early stage of ostogenesis," *Histochemistry* (Germany) 99(5):335–362 (1993).

Jelsma, T.N., et al., "Different forms of the neurotrosphin receptor trkB mRNA predominate in rat retina and optic nerve," *J. Neurobiol.* 24:1207–1214 (1993).

Johnson, J., et al., "BDNF supports survival of cultured rat retinal ganglion cells," *J. Neurosci.* 6:3031–3038 (1986).

Landreth, G.E. and B. W. Agranoff, "Explant Culture of Adult Goldfish Retina: Effect of Prior Optic Nerve Crush," *Brain Res.*, 118:299–303 (1976).

Maisonpierre, P.C., et al., "Neurotrophin–3: A neurotrophic factor related to NGF and BDNF," *Science* 247: 1446–1451 (1990).

Mansour–Robaey, S., et al., "Effects of ocular injury and administration of brain–derived neutrophic factor on survival and regrowth of axotomized retinal ganglion cells," *Proc. Natl. Acad. Sci.* 91:1632–1636 (1994).

Mey, J., et al., "Intravitreal injections of neurotrophic factors support the survival of axotomized retinal ganglion cells in adult rats in vivo," *Brain Research* 602:304–317 (1993).

Narang, S.A., et al., "Chemical Synthesis of Deoxyoligonucleotides by the Modified Triester Method," *Methods Enzymol.*, 65:610–620 (1980).

Schnell, L., et al., "Neutrophin–3 enhances sprouting of corticospinal tract during development and after adult spinal cord lesion," *Nature* 367:170–173 (1994).

Agrawal, Sudhir, et al., "Oligodeoxynucleoside phosphoramidates and phosphorothioates as inhibitors of human immunodeficiency virus," *Proc. Natl. Acad. Sci. USA* 85, 7079–7083 (1988).

(List continued on next page.)

*Primary Examiner*—Stephen G. Walsh
*Assistant Examiner*—Robert C Hayes
*Attorney, Agent, or Firm*—Pennie & Edmonds

[57] ABSTRACT

Cell culture conditions were developed which maintain the nerve cells of the retina in well-defined, serum-free conditions. The molecular factors that stimulate axonal regeneration from these neurons were characterized. The glial sheath cells that surround the axons of the optic nerve release two molecules that trigger and sustain nerve regeneration. One of the molecules is referred to as axogenesis factor 1 (AF-1), and is a low molecular weight polypeptide with a size in the range of 1000 daltons. The second molecule, AF-2, is a larger protein with a size of approximately 12,000 daltons. Studies indicate that these factors are strongly involved in CNS regeneration, and are therefore useful in the treatment of spinal cord and other nervous tissue damage.

1 Claim, 5 Drawing Sheets

OTHER PUBLICATIONS

Aizenman, Yair and Jean de Vellis, "Brain neurons develop in a serum and glial free environment: effects of transferrin, insulin, insulin–like growth factor–I and thyroid hormone on neuronal survival, growth and differentiation," Brain Res., 406:32–42 (1987).

Banker, G., and K. Goslin, eds. Culturing Nerve Cells (MIT Press, 1991)*.

Bastmeyer, Martin, et al., "Fish Optic Nerve Oligodendrocytes Support Axonal Regeneration of Fish and Mammalian Retinal Ganglion Cells," Glia, 8:1–11 (1993).

Bastmeyer, Martin, et al., "Growth of Regenerating Goldfish Axons Is Inhibited by Rat Oligodendrocytes and CNS Myelin but Not by Goldfish Optic Nerve Tract Oligodendrocytelike Cells and Fish CNS Myelin J. Neurosci, 11:626–640 (1991).

Bastmeyer, Martin, et al., "The spatiotemporal distribution of N–CAM in the retinotectal pathway of adult goldfish detected by the monoclonal antibody D3," Development, 108:299–311 (1990).

Battisti, W. P.,et al., "Temporal and spatial patterns of expression of laminin, chondroitin sulphate proteoglycan and HNK–1 immunoreativity during regeneration in the goldfish optic nerve," J. Neurocytol., 21:557–73 (1992).

Benowitz, Larry I., et al., "Specific Changes in Rapidly Transported Proteins During Regeneration of the Goldfish Optic Nerve," J. Neurosci., 1:300–307 (1981).

Benowitz, Larry I. and Lloyd A. Greene, "Nerve growth in the goldfish brain: biological assay studies using pheochromocytoma cells," Brain Res., 162:164–168 (1979).

Blaugrund, E., et al., "Immunological evidence that the neural adhesion molecule L1 is expressed in fish brain and optic nerve: possible association with optic nerve regeneration," Brain Res., 530:239–244 (1990).

Bottenstein (1983) In: Current Methods in Cellular Neurobiology, vol. IV: Model Systems. J.L. Barker and J.F. McKelvy, eds., 107–130 (John Wiley & Sons, New York)*.

Burrell, H.R., et al., "RNA metabolism in the goldfish retina during optic nerve regeneration," J. Neurochem., 31:289–298 (1978)*.

Caday, Cornelio G., et al. "Partial purification and characterization of a neurite–promoting factor from the injured goldfish optic nerve," Mol. Brain Res., 5:45–50 (1989).

Dichter, Marc A., "Rat Cortical Neurons in Cell Culture: Culture Methods, Cell Morphology, Electrophysiology, and Synapse Formation," Brain. Res., 149:279–293 (1978).

Doster, S. Kathleen, et al., "Expression of the Growh–Associated Protein GAP–43 in Adult Rat Retinal Ganglion Cells following Axon Injury," Neuron, 6:635–647 (1991).

Dowling, John E., et al. "White Perch Horizontal Cells in Culture: Methods, Morphology and Process Growth," Brain Res., 360;331–338 (1985).

Eitan, Shoshana and Michael Schwartz, "A Transglutaminase That Converts Interleukin–2 into a Factor Cytotoxic to Oligodendrocytes," Science, 261:106–108 (1993).

Eitan, Shoshana, et al., "Identification of an interleukin 2–like substance as a factor cytotoxic to oligodendrocytes and associated with central nervous system regeneration," Proc. Natl. Acad. Sci. USA, 89:5442–5446 (1992).

Finklestein, Seth P., et al., "Conditioned media from the injured lower vertebrate CNS promote neurite outgrowth from mammalian brain neurons in vitro," Brain Res., 413:267–274 (1987).

Giulian, Dana, et al., "Brain Peptides and Glial Growth, I., Glia–promoting Factors as Regulators of Gliogenesis in the Developing and Injured Central Nervous System," J. Cell Biol., 102:803–811 (1986a).

Giulian, Dana, et al., "Biosynthesis and Intra–axonal Transport of Proteins during Neuronal Regeneration," J. Biol. Chem., 255:6494–6501 (1980).

Giulian, Dana, "Isolation of Ganglion Cells from the Retina," Brain Research 189:135–155 (1980).

Giulian, Dana and Douglas G. Young, "Brain Peptides and Glial Growth. II. Identification of Cells That Secrete Glia–promoting Factors," J. Cell Biol., 102:812–820 (1986b).

Glasgow, Eric, et al., "Molecular cloning of gefiltin ($ON_1$): serial expression of two new neurofilament mRNAs during optic nerve regeneration," EMBO J., 13:297–305 (1994).

Glasgow, Eric, et al., "Plasticin, A Novel Type III Neurofilament Protein from Goldfish Retina: Increased Expression during Optic Nerve Regeneration," Neuron, 9:373–381 (1992).

Grafstein, B., "The retina as a regenerating organ," In R. Adler and B.D. Farber (Eds.), The Retina: A Model for Cell Biology Studies Part II, Academic Press, New York, 275–335*.

Grigoriev, M., et al., "A Triple Helix–forming Oligonucleotide–Intercalator Conjugate Acts as a Transcriptional Repressor via Inhibition of $NF_{\kappa}B$ Binding to Interleukin–2 Receptor α–Regulatory Sequence," The Journal of Biological Chemistry, 267:3389–3395 (1992).

Harada, Hidemitsu, et al., "Monoclonal antibody G6K12 specific for membrane–associated differentiation marker of human stratified squamous epithelia and squamous cell carcinoma," J. Oral Pathol. Med. (Denmark), 22(4):145–152 (1993).

Harel, A., et al., "Optic Nerve Regeneration in Adult Fish and Apolioprotein A–I," J. Neurochem., 52:1218–1228 (1989).

Heacock, Anne M. and Bernard W. Agranoff, "Protein Synthesis and Transport in the Regenerating Goldfish Visual System, Neurochem. Res., 7:771–788 (1982).

Holt, Jeffrey T., et al., "An Oligomer Complementary to c–myc mRNA Inhibits Proliferation of HL–60 Promyelocytic Cells and Induces Differentiation, Mol. Cell. Biol. 8, 963–973 (1988).

Hopkins, J.M., et al., "Laminin and Optic Nerve Regeneration in the Goldfish," J. Neurosci. 5:3030–3038 (1985).

Itakura, Keiichi, et al., "Synthesis and Use of Synthetic Oligonucleotides," Ann. Rev. Biochem. 53:323–356 (1984).

Johnson, James E. and James E. Turner, "Growth From Regenerating Goldfish Retinal Cultures in the Absence of Serum or Hormonal Supplements: Tissue Extract Effects," J. Neurosci. Res., 8:315–329 (1982).

Koren, Eugen, et al., "Characterization of a monoclonal antibody that binds equally to all apolipoprotein and lipoprotein forms of human plasma apolipoprotein B.1. Specificity and binding studies," Biochim. Biophys. Acta 876:91–100 (1986).

LaBate, Michael E. and J. H. Pate Skene, "Selective Conservation of GAP–43 Structure in Vertebrate Evolution, Neuron, 3:299–310 (1989).

Landreth, G.E. and B. W. Agranoff, "Explant Culture of Adult Goldfish Retina: A Model for the Study of CNS Regeneration," Brain Res., 161:39–53 (1979).

Lima, L., et al., "the Interaction of Substrate and Taurine Modulates the Outgrowth From Regenerating Goldfish Retinal Explants," *Int. J. Devl. Neuroscience* 7:375–382 (1989).

McQuarrie, Irvine G. and Bernice Grafstein, "Effect of a Conditioning Lesion on Optic Nerve Regeneration in Goldfish," *Brain Research*, 216:253–264 (1981).

Merrifield, R.B., "Solid Phase Peptide Synthesis. I. The Synthesis of a Tetrapeptide," *J. Am. Chem. Soc.* 85, 2149 (1964).

Meyer, Ronald L., et al., "Topography of Regenerating Optic Fibers in Goldfish Traced With Local Wheat Germ Injections Into Retina: Evidence for Discontinuous Microtopography in the Retinotectal Projection," *J. Comp. Neurol.*, 239:27–43 (1985).

Mizrachi, Yaffa, et al., "A Neurotrophic Factor Derived from Goldfish Brain: Characterization and Purification," *J. Neurochem.*, 46:1675–1682 (1986).

Moya, Kenneth L., et al., "Changes in Rapidly Transported Proteins in Developing Hamster Retinofugal Axons," *J. Neurosci.*, 8:4445–4454 (1988).

Mulder, Arend, et al., "Characterization of Two Human Monoclonal Antibodies Reactive with HLA–B12 and HLA–B60, Respectively, Raised by in vitro Secondary Immunization of Peripheral Blood Lymphocytes," *Hum. Immunol.*, 36(3):185–192 (1993).

Mulligan, Richard C., " The Basic Science of Gene Therapy," *Science*, 260, 926–932 (1993).

Murray, Marion and David S. Forman, "Fine Structural Changes in Goldfish Retinal Ganglion Cells During Axonal Regeneration," *Brain Res.*, 32:287–298 (1971).

Murray, Marion and Bernice Grafstein, "Changes in the Morphology and Amino Acid Incorporation of Regenerating Goldfish Optic Neurons," *Exp. Neurol.*, 23:544–560 (1969).

Offensperger, Wolf–Bernhard, et. al., "In vivo inhibition of duck hepatitis B virus replication and gene expression by phosphorothioate modified antisense oligodeoxynucleotides," *EMBO J.* 12, 1257–1262 (1993).

Orson, F., et al., "Oligonucleotide inhibition of IL2R$\alpha$ mRNA transcription by promoter region collinear triplex formation in lymphocytes," *Nucleic Acids Research*, 19:3435–3441 (1991).

Paschke, Katja A., et al., "Neurolin, a Cell Surface Glycoprotein on Growing Retinal Axons in the Goldfish Visual System, Is Reexpressed during Retinal Axonal Regeneration," *J. Cell Biol.*, 117:863–875 (1992).

Perrone–Bizzozero, Nora I., and Larry I. Benowitz, "Expression of a 48–Kilodalton Growth–Associated Protein in the Goldfish Retina," *J. Neurochem.*, 48:644–652 (1987).

Perry, G.W., et al., "Fast Axonally Transported Proteins in Regenerating Goldfish Optic Axons," *J. Neurosci.*, 7:792–806 (1987).

Quitschke, Wolfgang and Nisson Schechter, "Specific Optic Nerve Proteins During Regeneration of the Goldfish Retinotectal Pathway," *Brain Res.*, 1–10 (1982).

Reichardt, L.R. and K.J. Tomaselli, "Extracellular matrix molecules and their receptors: Functions in the neural development," *Ann. Rev. Neurosci.*, 14:531–70 (1991)*.

Salles, Fernando J., et al., "A plasminogen activator is induced during goldfish optic nerve regeneration," *EMBO J.*, 9:2471–2477 (1990).

Sarin, Prem S., et al., "Inhibition of acquired immunodeficiency syndrome virus by oligodeoxynucleoside methylphosphonates," *Proc. Natl. Acad. Sci. USA* 85:7448–7451 (1988).

Schmidt, John T., et al., "Ependymin as a Substrate for Outgrowth of Axons from Cultured Explants of Goldfish Retina," *J. Neurobiol.* 22:40–54 (1991).

Schwab, Martin E. and Pico Caroni, "Oligodendrocytes and CNS Myelin Are Nonpermissive Substrates for Neurite Growth and Fibroblast Spreading in vitro," *J. Neurosci.*, 8:2381–2393 (1988).

Schwartz, Michael and Bernard W. Agranoff, "Outgrowth and Maintenance of Neurites from Cultured Goldfish Retinal Ganglion Cells," *Brain Research* 206:331–343 (1981).

Schwartz, M., et al., "Regenerating Fish Optic Nerves and a Regeneration–Like Response in Injured Optic Nerves of Adult Rabbits," *Science*, 228:660–603 (1985).

Shashoua, Victor E., "The Role of Brain Extracellular Proteins in Neuroplasticity and Learning," *Cell. Mol. Neurobiol.*, 5:183–207 (1985).

Shaw, Jeng–Pyng, et al., "Modified deoxyoligonucleotides stable to exonuclease degradation in serum," *Nucleic Acids Res* 19:747–750 (1991).

Sivron, T., et al., "Presence of Growth Inhibitors in Fish Optic Nerve Myelin: Postinjury Changes," *J. Comp. Neurol.*, 343:237–246 (1994).

Skene, J. H. Pate and Mark Willard, "Changes in Axonally Transported Proteins during Axon Regeneration in Toad Retinal Ganglion Cells," *J. Cell Biol.*, 89:86–95 (1981).

Skene, J.H. Pate and Mark Willard, *J. Cell. Biol.*, 89:96–103* (1981).

Sperry, R.W., "Optic Nerve Regeneration with Return of Vision in Anurans,38 *J. Neurophysiol.* 7:57–69 (1944).

Sperry, R.W., "Chemoaffinity in the Orderly Growth of Nerve Fiber Patterns and Connections," *Proc. Nat. Acad. Sci. USA*, 50:703–710 (1963).

Stauber, N., et al., (May 26, 1993) *J. Immunol. Methods* (Netherlands), 161(2): 157–168*.

Thormodsson, F.R., et al., "Immunochemical Studies of Extracellular Glycoproteins (X–GPs) of Goldfish Brain," *Exp. Neurol.*, 118:275–283 (1992).

Turner, James E., et al., "Nerve Growth Factor Stimulates Neurite Outgrowth from Goldfish Retinal Explants: The Influence of a Prior Lesion," *Dev. Brain Res.*, 4:59–66 (1982).

Turner, James E., et al., "Retinal Ganglion Cell Response to Axotomy and Nerve Growth Factor Antiserum Treatment in the Regenerating Visual System of the Goldfish (*Carassim auratus*): An In Vivo and In Vitro Analysis *Brain Res.*, 204:283–294 (1981).

Venkateswaran, Subramaniam, et al., "Production of Anti––Fibroblast Growth Factor Receptor Monoclonal Antibodies by In Vitro Immunization," *Hybridoma*, 11(6):729–739 (1992).

Vielmetter, Jost, et al., "The Monoclonal Antibody E587 Recognizes Growing (New and Regenerating) Retinal Axons in the Goldfish Retinotectal Pathway," *J. Neurosci*, 11:3581–3593 (1991).

Walicke, Patricia, et al. "Purification of a Human Red Blood Cell Supporting the Survival of Cultured CNS Neurons, and Its Identification as Catalase," *J. Neurosci.*, 6:1114–1121 (1986).

Wickstrom, et al., "Human promyelocytic leukemia HL–60 cell proliferation and c–myc protein expression are inhibited by an antisense pentadecadeoxynucleotide targeted against c–myc mRNA," *Proc. Natl. Acad. Sci. USA* 85, 1028–1032 (1988).

Wilmot, George R., et al., "The Expression of the Protein p68/70 within the Goldfish Visual System Suggests a Role in Both Regeneration and Neurogenesis," *J. Neurosci.*, 13:387–401 (1993).

Yip, Henry K. and Bernice Grafstein, "Effect of Nerve Growth Factor on Regeneration of Goldfish Optic Axons," *Brain Res.* 238:329–339 (1982).

Zamecnik, Paul C. and Mary L. Stephenson, "Inhibition of Rous sarcoma virus replication and cell transformation by a specific oligodeoxynucleotide," *Proc. Natl. Acad. Sci. USA* 75, 280–284 (1978).

Zamecnik, Paul C., et al., "Inhibition of replication and expression of human T–cell lymphotropic virus type III in cultured by exogenous synthetic oligonucleotides complementary to viral RNA," *Proc. Natl. Acad. Sci.*, 83, 4143–4146 (1986).

Zhu, Ning, et al., "Systemic Gene Expression After Intravenous DNA Delivery into Adult Mice," *Science* 261, 209–211 (1993).

Shea et al Neurosci Res. Comm. 13 1–7 (1993).

Shea Neurosci Res. Comm. 15 119–123 (1994).

Giulian PNAS 81 3567–71 (1984).

Giulian et al S Neurosci 13 29–37 (1993).

Le Roux et al S Neurosci 14 4639–4655 (1994).

Assouline et al Dev Brain Res. 31 103–118 (1987).

Davis et al Amn NY Acad Sci 486 194–205 (1986).

Matthiessen et al Glia 2 177–88 (1989).

Cochran et al Dev Brain Res. 17 105–116 (1985).

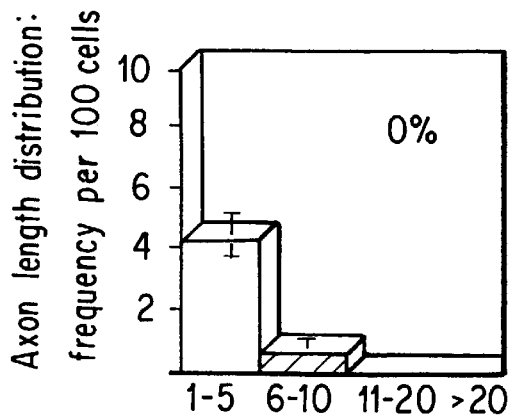
FIG.1A1
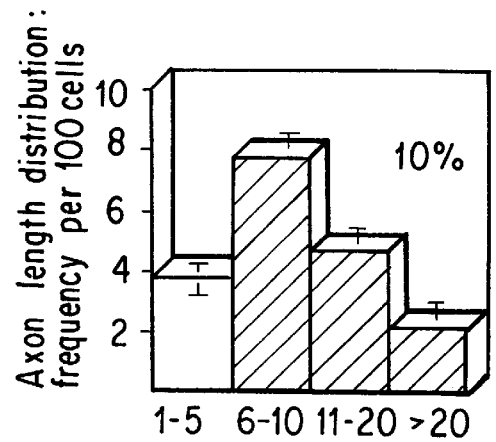
FIG.1A3
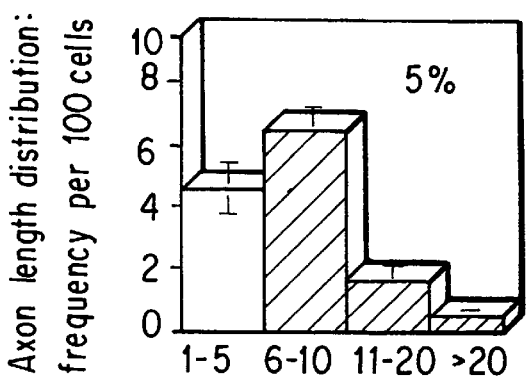
FIG.1A2
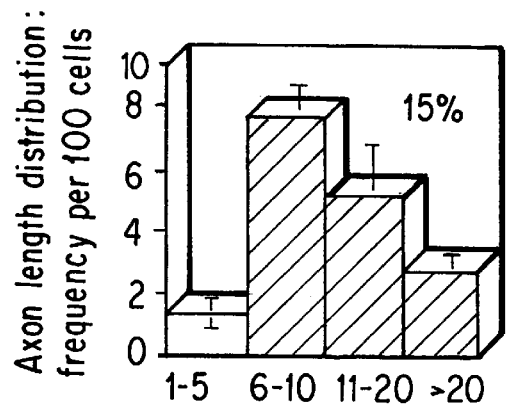
FIG.1A4

TROPHIC FACTORS FOR CENTRAL NERVOUS SYSTEM REGENERATION

The United States government has certain rights in this invention by virtue of National Institutes of Health Grant No. RO1 EY 05690 to Larry Benowitz.

BACKGROUND OF THE INVENTION

The present invention is generally in the area of methods and treatments for central nervous system injury, and particularly the use of trophic factors for spinal cord regeneration.

Past early childhood, injury to the central nervous system (CNS) results in functional impairments that are largely irreversible. Within the brain or spinal cord, damage resulting from stroke, trauma, or other causes can result in life-long losses in cognitive, sensory and motor functions, and even maintenance of vital functions. Nerve cells that are lost are not replaced, and those that are spared are generally unable to regrow severed connections, although a limited amount of local synaptic reorganization can occur close to the site of injury. Functions that are lost are currently untreatable.

Regenerative failure in the CNS has been attributed to a number of factors, which include the presence of inhibitory molecules on the surface of glial cells that suppress axonal growth; absence of appropriate substrate molecules such as laminin to foster growth; and an absence of the appropriate trophic factors needed to activate programs of gene expression required for cell survival and differentiation.

By contrast, within the peripheral nervous system (PNS), injured nerve fibers can regrow over long distances, with eventual excellent recovery of function. Within the past 15 years, neuroscientists have come to realize that this is not a consequence of intrinsic differences between the nerve cells of the peripheral and central nervous system; remarkably, neurons of the CNS will extend their axons over great distances if given the opportunity to grow through a grafted segment of PNS (e.g., sciatic nerve). Therefore, neurons of the CNS retain a capacity to grow if given the right signals from the extracellular environment. Factors which contribute to the differing growth potentials of the CNS and PNS include partially characterized, growth-inhibiting molecules on the surface of the oligodendrocytes that surround nerve fibers in the CNS, but which are less abundant in the comparable cell population of the PNS (Schwann cells); molecules of the basal lamina and other surfaces that foster growth in the PNS but which are absent in the CNS (e.g., laminin); and trophic factors, soluble polypeptides which activate programs of gene expression that underlie cell survival and differentiation. Although such trophic factors are regarded as essential to maintaining the viability and differentiation of nerve cells, the particular ones that are responsible for inducing axonal regeneration in the CNS remain uncertain.

In contrast to man and other higher vertebrates, lower vertebrates are able to regenerate injured CNS pathways throughout life (Sperry, R. W. (1944), *J. Neurophysiol.*, 7:57–69; Sperry, R. W. (1963), *Proc. Nat. Acad. Sci. USA*, 50:703–710). In the goldfish, 95% of retinal ganglion cells survive injury to the optic nerve (Meyer, et al., (1985), *J. Comp. Neurol.*, 239:27–43) and go on to re-establish topographically organized, functional connections with cells of the optic tectum and other target areas within one to two months (reviewed in Grafstein, (1986), The retina as a regenerating organ, In R. Adler and B. D. Farber (Eds.), The Retina: A Model for *Cell Biology Studies Part II*, Academic Press, New York, 275–335; Jacobson, (1991), Development Neurobiology, third edition (Plenum Publishing Co., New York)). The cellular and molecular changes that accompany this process have been studied in depth. Retinal ganglion cells undergo extensive metabolic and morphological changes that include a dramatic enlargement of the nucleolus, a proliferation of free ribosomes, and an increase in cell diameter (Murray & Grafstein, (1969), *Exp. Neurol.*, 23:544–560; Murray & Forman, 1971 (1971), *Brain Res.*, 32:287–298). Massive increases are seen in the expression of genes encoding certain components of the cytoskeleton (Burrell, et al., (1978), *J. Neurochem.*, 31:289–298; Heacock & Agranoff, (1982), *Neurochem. Res.*, 7:771–788; Giulian, et al., (1980), *J. Biol. Chem.*, 255:6494–6501; Quitschke & Schechter, (1983), *Brain Res.*, 258:69–78; Glasgow, et al., (1994) *EMBO J.*, 13:297–305; Glasgow, et al. (1992) *Neuron*, 9:373–381), cell surface adhesion molecules (Vielmetter, et al., (1991) *J. Neurosci*, 11:3581–3593; Bastmeyer, et al., (1990) Development, 108:299–311; Paschke, et al., (1992) *J. Cell Biol.*, 117:863–875; Blaugrund, et al., 1990; Battisti, et al., (1992) *J. Neurocytol.*, 21:557–73), and several proteins that become incorporated into the growing nerve terminal membrane, particularly GAP-43 (Benowitz, et al., (1981) *J. Neurosci.*, 1:300–307; Heacock & Agranoff, (1982); Perrone-Bizzozero, et al., (1987), *J. Neurochem.*, 48:644–652; Perry, et al., (1987), *J. Neurosci.*, 7:792–806; LaBate & Skene, (1989), *Neuron*, 3:299–310; Wilmot, et al., (1993), *J. Neurosci.*, 13:387–401). Some of the same changes are associated with the development and regeneration of the optic nerve in other species (Skene & Willard, (1981), *J. Cell Biol.*, 89:86–95 *J. Cell. Biol.*, 89:96–103; Moya, et al., (1988), *J. Neurosci.*, 8:4445–4454; Doster, et al., (1991), *Neuron*, 6:635–647).

In general, the capacity of neurons to regenerate their axons after injury is strongly influenced by the surrounding non-neuronal elements (Aguayo, et al., (1991) *Phil. Trans. Royal Soc. London, Series B*, 331:337–343). In the case of the goldfish retinofugal pathway, the glial sheath cells of the optic nerve seem to provide an environment that is highly conducive to axonal outgrowth (Bastmeyer, et al., (1993) *Glia*, 8:1–11; Bastmeyer, et al., (1991) *J. Neurosci*, 11:626–640). In part, this may be attributed to the expression of particular cell surface and extracellular matrix proteins, including an L1-like cell adhesion molecule (Blaugrund, et al., (1990) *Brain Res.*, 530:239–244; Bastmeyer, et al., (1993); Bastmeyer, et al. (1991); Vielmetter, et al., 1991; Battisti, et al., 1992), laminin (Hopkins, et al., (1985) *J. Neurosci.*, 5:3030–3038), and chondroitin sulfate proteoglycans (Battisti, et al., 1992). At the same time, optic nerve glia of goldfish seem to express lower levels of growth-inhibiting proteins on their surfaces than mammalian CNS oligodendrocytes (Caroni & Schwab, (1988) *J. Cell Biol.*, 106:1281–1288; Schwab & Caroni, (1988) *J. Neurosci.*, 8:2381–2393; Bastmeyer, et al., 1991; Sivron, et al., (1994), Presence of growth inhibitors in fish optic nerve myelin: postinjury changes. *J. Comp. Neurol.*, 343:237–246).

In addition to cell surface components, cells of the goldfish optic nerve secrete soluble factors that promote axonal outgrowth from goldfish retinal explants (Mizrachi, et al., (1986) *J. Neurochem.*, 46:1675–1682), embryonic mammalian neurons (Finkelstein, et al., (1987) *Brain Res.*, 413:267–274; Caday, et al., 1989), and the mature rabbit retina (Schwartz, et al., (1985) *Science*, 228:600–603). Among the proteins that are secreted by the glia and microphages of the optic nerve are apolipoprotein A (Harel, et al., (1989) *J. Neurochem.*, 52:1218–1228), a plasminogen activator (Salles, et al., (1990) *EMBO J.*, 9:2471–2477), interleukin-2 (Eitan, et al., 1992), a transglutaminase (Eitan and Schwartz, (1993) *Science*, 261:106–108), and platelet-derived growth factor (Eitan, et al., (1992) *Proc. Natl. Acad. Sci. USA*, 89:5442–5446).

Despite these findings, the factors responsible for initiating axonal outgrowth from retinal ganglion cells remain unknown. Studies directed towards this issue have generally been carried out either in vivo or have utilized retinal explants derived from animals in which regeneration had already been triggered in vivo by a conditioning lesion (Landreth and Agranoff (1976) Brain Res., 118:299–303; Landreth and Agranoff (1979) Brain Res., 161:39–53; Turner, et al., (1981) Brain Res., 204:283–294; Turner, et al. (1982) Dev. Brain Res., 4:59–66; Schwartz, et al., 1985; Yip & Grafstein, (1982) Brain Res., 238:329–339; Hopkins, et al., 1985; Lima, et al., (1989) *Int. J. Devl. Neuroscience*, 7:375–382). The fact that various agents tested fail to augment outgrowth unless the regenerative process had already begun in vivo suggests that the factors required to initiate regeneration may derive from a source that is absent in the explant cultures, e.g., the optic nerve glia, the circulatory system, or other brain tissue (Johnson and Turner, (1982) *J. Neurosci. Res.*, 8:315–329). Trophic factors are generally reviewed in Developmental Neurobiology, M. Jacobson (Third Edition, Plenum Publ. Co., NY 1991, Chapters 8 and 11); Molecular Neurobiology, Z. Hall, editor (Sinauer Publ. Co., Sunderland, Mass. 1992, Chapters 11 and 12).

It is therefore an object of the present invention to provide a method for obtaining molecular signals that initiate regeneration of nerve connections in mammals.

It is a further object of the present invention to provide factors which initiate regeneration of nervous tissue in mammals.

It is another object of the present invention to provide methods for treatment of injuries to spinal cord and other central nervous system tissue.

SUMMARY OF THE INVENTION

Cell culture conditions were developed which maintain the nerve cells of the retina in well-defined, serum-free conditions. The molecular factors that stimulate axonal regeneration are released from the glial cells that surround the nerve fibers. These were characterized. The glial sheath cells that surround the axons of the optic nerve release two molecules that trigger and sustain nerve regeneration. One of the molecules is referred to as axogenesis factor 1 (AF-1), and is a low molecular weight polypeptide with a size in the range of 1000 daltons. The second molecule, AF-2, is a larger protein with a size of approximately 12,000 daltons. Studies indicate that these factors are strongly involved in CNS regeneration, and should therefore be useful in the treatment of optic nerve, brain, spinal cord and other nervous tissue damage.

BRIEF DESCRIPTION OF THE DRAWINGS

FIGS. 1A1, 1A2, 1A3 and 1A4 are histograms of the quantitation of neurite outgrowth: axon length distribution was measured five days after nerve cells were cultured with CM at the indicated concentrations of 0%, 5%, 10% and 15%, as shown in FIGS. 1A1, 1A2, 1A3 and 1A4, respectively. Number of cells extending processes 1–5 cell diameter in length (light shading); number extending processes greater than 5 cell diameter in length (dark shading). Values represent averages from 4 wells for each CM concentration; error bars show ±standard error of the mean (SEM).

FIG. 2a is CM obtained from previously intact optic nerves (day 0) or from optic nerves which had been injured 3 or 7 days previously, separated into high and low molecular weight fractions by ultrafiltration (3,000 Da cut-off). In all cases, both low (light shading) and high (dark shading) molecular weight fractions yielded high levels of neurite-promoting activity. FIG. 2b compares control with CM and CM separated with a molecular weight cut-off of 1,000 Da.

FIG. 3 is a graph of neurite outgrowth showing that the low molecular weight factor, AF-1, can be isolated using a two-phase solvent extraction system. The negative control is culture medium alone; the positive control, lane 2, is the low molecular weight fractions of the molecules secreted by the glial sheath cells into culture medium, CM less than 3,000 Da, which induces high levels of axonal growth. When this material is mixed with an organic solvent at pH 7.5, isobutanol, little activity remains in the aqueous phase (pH 7.5 Aq). When the organic phase is then mixed with a low pH buffer (pH2 Aq), the biologically active molecule goes into the aqueous phase and nothing remains in the organic phase, (pH2 org).

FIG. 4 is a graph of neurite outgrowth showing that when the partially purified extract containing the low molecular weight trophic factor, AF-1, is separated by reversed phase HPLC, the active component appears in particular column fractions (FC, FD, FE). As in FIG. 3, the negative control (L-15) is the tissue culture medium alone; the positive control is the unfractionated low molecular weight component of the molecules secreted by optic nerve glia (1CM less than 3,000 Da, 10% concentration); FA-FI indicate column fractions from the high performance liquid chromatography separation.

DETAILED DESCRIPTION OF THE INVENTION

Figure 1B:
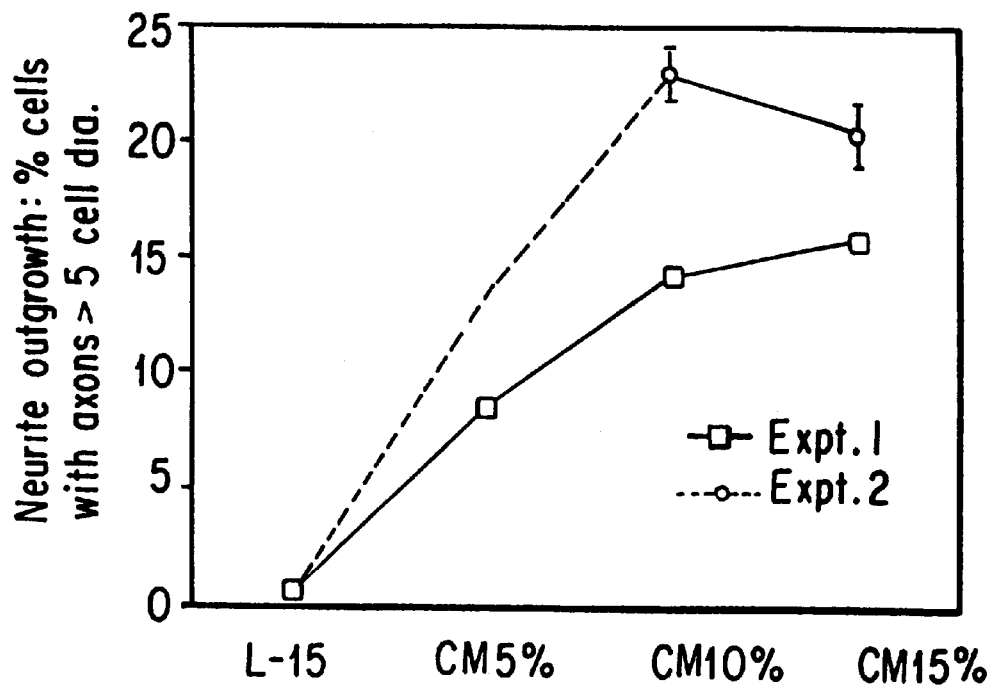
FIG. 1b are dose-response curves of 2 separate experiments showing neurite outgrowth (% cells with axons greater than 5 cell diameters) in response to increasing concentrations of CM (0%, 5%, 10%, and 15%). Data represent the percentage of cells with processes greater than 5 cell diameter in length, a cut-off point selected based upon the histogram data in FIG. 1a. In both experiments, maximal outgrowth is attached in response to CM at a 10% concentration (i.e., total protein concentration of about 10 μg/ml). Error bars are not shown if less than 1%.

I. Discovery of the Molecular signals that Initiate Nerve Regeneration

The capacity of lower vertebrates to regrow an injured optic nerve has been the subject of numerous studies aimed at understanding CNS development and plasticity. To characterize the endogenous factors that induce retinal ganglion cells to regenerate their axons, a dissociated model of the goldfish retina cultured in serum-free, defined media has been developed. Under these conditions, retinal ganglion cells extend lengthy, axon-like processes in response to two soluble factors that derive from cells of the goldfish optic nerve. One of these, tentatively named axogenesis factor 1 (AF-1), is a small, heat-stable, protease-sensitive molecule which passes through a 1 kDa cut-off filter; the second, AF-2, is a heat-labile protein with an estimated size of 8–15 kDa.

These studies were conducted as follows. Three days after crushing the optic nerve behind the orbit, optic nerves and tracts were removed, cut into 0.5 to 1 mm pieces, and incubated in HEPES-buffered L15 medium for 3 to 4 h. This conditioned medium was filtered and subjected to ion-exchange, HPLC reversed-phase and size-exclusion chromatography to purify factor(s) that induce neurite outgrowth from dissociated retinal neurons in culture. Cultures were obtained by dissecting retinas from normal goldfish, treating with papain for 45 minutes, triturating gently, and sedimenting out large pieces of tissue. Outgrowth was scored blind in 3 to 6 wells per condition based on the fraction of large, viable cells extending neurites greater than or equal to 5 cell diameter after 5 days in culture, with viability assessed using 5(6)-carboxyfluorescein diacetate.

A several-fold increase in neurite outgrowth was induced by a trypsin-sensitive, heat-stable, basic protein, $M_r$=10 to 15 kDa. A second, distinct peak of neurite-promoting activity has a $M_r$ of less than 1,000 kDa. These studies indicated that the goldfish optic nerve secretes multiple trophic factors that may make distinct contributions to axonal outgrowth.

As described herein, under baseline conditions, cells remained viable for at least a week but showed little outgrowth, as assessed using the vital dye 5,6-carboxyfluorescein diacetate (5,6-CFDA). Addition of conditioned medium (CM) containing molecules secreted by the support cells of the optic nerve (AF-1 and/or AF-2) induced up to 25% of neurons to extend processes greater than or equal to 5 cell diameters in length after five to six days. In some instances, this growth exceeded 300 $\mu$m. To verify that this outgrowth was from retinal ganglion cells (RGCs) per se, the lipophilic dye 4-Di-10 ASP was applied to the optic tectum 5 to 7 days before dissecting retinas. After six days in culture, cells that were retrogradely labeled with 4-Di-10 ASP showed twice as much neurite outgrowth as the overall population, indicating that CM acts upon RGCs selectively. The effect of CM was shown not to be secondary to enhanced viability, since neither the percentage of 4-Di-10 ASP-labeled cells in the total population nor overall cell survival was affected by the presence of CM.

AF-1 and AF-2 do not seem to coincide with any of the molecules identified previously in CM from the goldfish optic nerve. Mizrachi, et al. (1986) described a 10 kDa protein in optic nerve CM which binds to DEAE at neutral pH and which is adsorbed onto polylysine substrate. This protein enhanced neurite outgrowth in retinal explants which had begun to regenerate their axons in vivo, but did not induce outgrowth from unprimed retinas. AF-2, in addition to inducing outgrowth from unprimed retinal ganglion cells, does not bind to DEAE even at pH 8.4 and is not adsorbed onto substrate. Other components of CM that also differ from the ones described here include apolipoprotein A, a 28 dDa protein that binds to heparin sulfate proteoglycans and which may contribute to lipid transport (Harel, et al., 1989); a 60–65 kDa plasminogen activator that may be involved in the proteolysis of the extracellular matrix, thereby allowing growing axons to advance (Salles, et al., 1990); a 28 kDa protein resembling interleukin-2 (IL-2; Eitan, et al., 1992); a transglutaminase that may contribute to the dimerization of IL-2, rendering it toxic to oligodendrocytes (Eitan & Schwartz, 1993); platelet-derived growth factor (Eitan, et al., 1992); an acidic 26 kDa protein that binds to polylysine substrate and induces embryonic mammalian neurons to extend long, unbranched axons (Caday, et al. (1989) *Mol. Brain Res.*, 5:45–50); and laminin, a 106 kDa glycoprotein which is a major constituent of the extracellular matrix (Hopkins, et al., 1985; Battisti, et al., 1992; Reichardt and Tomaselli, (1991) *Ann. Rev. Neurosci.*, 14:531–70); Giulian, et al. (1986a) *J. Cell Biol.*, 102:803–811; Giulian and Young (1986b) *J. Cell Biol.*, 102:812–820; have described polypeptides of 3, 6, 9 and 125 kDa that are secreted by the tectum after optic nerve injury and which contribute to the proliferation of particular macroglial populations of the nerve. Finally, a group of glycoproteins with molecular weights greater than or equal 37 kDa (ependymins or X-GPs), which are secreted by cells of the choroid plexus (Thormodsson, et al., (1992) *Exp. Neurol.*, 118:275–283) and the subependymal layer (Shashoua, (1985) *Cell. Mol. Neurobiol.*, 5:183–207), have been shown to promote axonal outgrowth in primed explants (Schmidt, et al., 1991). The fact that molecules matching these properties were not found to be active in our system suggests either that (a) their effects upon RGCs are too subtle to detect in our assay, (b) they may only work on RGCs which had been primed first in vivo, or (c) their primary effects are upon another cell type which acts upon RGCs secondarily.

II. Characterization of Trophic Factors

Size-separation studies revealed that CM contains two active components. The first molecule, named axogenesis factor 1 (AF-1), passes through a 1 kDa cut-off filter. It is heat resistant but sensitive to proteinase K digestion. The second molecule, AF-2, has a size of 8 to 15 kDa and is heat labile and trypsin sensitive. AF-1 is considerably more concentrated in CM than in optic nerve homogenates, suggesting that it is actively secreted; AF-2 has a similar concentration intra- and extracellularly.

The two factors induce vigorous neurite outgrowth from RGCs regardless of whether the regenerative response had been initiated in vivo by a priming lesion. Moreover, ganglion cells primed to grow by a conditioning lesion show essentially no outgrowth in the absence of either factor. Thus, under the experimental conditions used here, AF-1 and/or AF-2 is required to induce and maintain axonal regeneration.

The goldfish optic nerve consists of several cell types, including oligodendroglia, astrocytes, macrophages, microglia, and epithelial cells (Battisti, et all., 1992). The trophic factors could be secreted from any of these or, alternatively, they might only be released from the cytoplasm of cells injured by nerve crush or by dissection in culture. To address this issue, the concentration of the two factors in conditioned media and in cytosol fractions prepared from optic nerve homogenates were compared. AF-1 was found to be present in significantly higher concentrations in CM than in optic nerve cytosol, suggesting that it is actively secreted. AF-2, on the other hand, was present at similar concentrations intra- and extracellularly. If most of the proteins in CM are a consequence of cell lysis, then a protein that is present in equal concentrations intra- and extracellularly may normally be present only within cells, though physiologically it could still appear extracellularly after nerve injury. However, if most of the proteins that are present extracellularly derive from active secretory mechanisms, then AF-2 might normally be secreted physiologically. Studies done in collaboration with Dr. C. Stürmer (University of Konstanz, Germany) indicated that media containing factors secreted from dissociated goldfish optic nerve glia contains appreciable levels of a trophic factor of less than 3,000 Da, and lower levels of one greater than 3,000 Da. These findings indicated that it is the glial cells of the optic nerve that are the source of AF-1 and AF-2, and not damaged axons or blood. The latter source is also rendered unlikely by the absence of neurite-promoting activity in media conditioned by a variety of other tissues.

Characterization of AF-1 and AF-2

AF-1 and AF-2 were initially characterized by determination of the presence of trophic activity after passage of material through molecular weight filters or sieves of specific molecular weight. Several methods were used to determine the size of the active factors. CM was first separated by centrifugal ultrafiltration using filters with molecular weight cut-offs of 10, 100, and 1000 kDa. Filtrates and retentates were tested in the bioassay. Next, CM was passed through a 6,000 Da desalting column and fractions were monitored by absorbance at 280 nm (for protein) and by measuring conductivity (for low-molecular weight fractions containing salts). Fractions containing high and low molecular weight constituents were evaluated by bioassay and were both found to be active. Fractions greater than 6,000 Da were pooled, concentrated 10- to 100-fold using a filter with a 3,000 Da cut-off, then separated by high performance liquid chromatography (HPLC). The low molecular weight material, less than 6,000 Da, was characterized further by being passed through a filter with a 1,000 Da molecular weight cut-off.

Anion-exchange chromatography of the trophic factors, for example, on diethylaminoethyl cellulose columns, was then carried out. The column was initially washed with 25 mM HEPES, then stepwise eluted with 0.1, 0.2, 0.5 and 1.0M NaCl in 25 mM HEPES.

The purification of AF-1 and AF-2 based on molecular weight and anion exchange chromatography, as described herein, is sufficient to obtain amino acid sequence which is used to generate oligonucleotide probes for the screening of gene libraries for clones encoding the trophic factors.

For example, samples of purified AF-1 are being submitted to the Harvard University Microchemistry Facility for determination of the amino acid composition and exact molecular weight by mass spectroscopy, for approximately $200 per sample. This facility can microsequence polypeptides for about $250–$1,000 per sample. Childrens' Hospital has a facility which can generate multiple oligonucleotides that encode the peptide sequence, allowing for the degeneracy in the genetic code. These oligonucleotides will be radiolabeled and used to screen a cDNA library to isolate the genes that encode the polypeptide from which AF-1 derives. This will then be sequenced to determine whether it encodes the correct amino acid sequence for AF-1.

Once sequenced, the proteins can be made by expression of recombinant sequences in cell culture, isolation of naturally occurring trophic factors, or, preferably in the case of AF-1, by synthetic means. These methods are known to those skilled in the art. An example is the solid phase synthesis described by J. Merrifield, *J. Am. Chem. Soc.* 85, 2149 (1964), used in U.S. Pat. No. 4,792,525, and described in U.S. Pat. No. 4,244,946, wherein a protected alpha-amino acid is coupled to a suitable resin, to initiate synthesis of a peptide starting from the C-terminus of the peptide. Other methods of synthesis are described in U.S. Pat. Nos. 4,305,872 and 4,316,891. These methods can be used to synthesize peptides having identical sequence to the trophic factors described herein, or substitutions or additions of amino acids, which can be screened for activity as described above and in the following examples.

III. Use in Diagnostic, Screening, and Isolation of Trophic Factors.

Evolutionary conservation and Isolation of other trophic factors.

Research over the past ten years or so has clearly shown that the molecular elements that underlie the development and functioning of the nervous system are phylogenetically ancient and highly conserved throughout vertebrate evolution. Molecules such as transcription factors controlling programs of gene expression, known trophic factors, cell recognition molecules, transmitters and their receptors have remained remarkably unaltered over the last several hundred million years, and it is therefore predictable that homologous equivalents of AF-1 and AF-2 exist in the nervous system of higher vertebrates, including humans, and can be identified based on the analogous structures and sequences of the fish trophic factors initially described herein. Moreover, although these molecules were studied in the visual system, the retina and optic nerve develop ontogenetically as extensions of the midbrain and are essentially identical to other portions of the central nervous system. It is therefore expected that AF-1 and AF-2 will act upon other populations of neurons besides the retinal ganglion cells, especially the spinal cord and cerebral cortex in mammals. Injury to neurons in the cerebral cortex is the principal factor in stroke, while failure of spinal cord neurons to regenerate damaged axons is the major factor in many types of paralysis that result from accidents.

Confirmation of the broad specificity of the factors can be established using a primary culture system of dissociated neurons from the rat spinal cord, for example, as described by G. Banker and K. Goslin, eds. *Culturing Nerve Cells* (MIT Press, 1991). This system can then be used to study whether AF-1 or AF-2 influences the outgrowth of axons from all of the cell types in culture, essentially paralleling the approach used in the following examples using retinal ganglion cells.

Confirmation of these results can be obtained using an in vivo model to investigate the effect of AF-1 and AF-2, for example, a mammalian spinal cord injury model. The spinal cord is transected through the dorsal columns, after which AF-1 or AF-2 is delivered either through the use of a minipump or by embedding them in slow-release capsules, as described in more detail below.

As used herein, unless specifically stated otherwise, the terms "AF-1" and "AF-2" refer to the respective proteins purified as described herein, and degenerate variants thereof and their equivalents in other species of origin, especially human, as well as functionally equivalent variants, having additions, deletions, and substitutions of amino acids which do not significantly alter the functional activity of the neurotrophic factors as characterized above.

Diagnostic and Screening Applications

The understanding of the structure and functions of the trophic factors described herein, as well as the cDNAs encoding these proteins and antibodies immunoreactive therewith, have a variety of uses. Specifically, the proteins and their DNAs can be used not only in the treatment of patients as described below, but in screening of drugs which modulate the activity and/or the expression of the trophic factors and in screening of patient samples for the presence of functional trophic factor; use of the DNA to construct probes for screening of libraries for other trophic factors, including the human equivalents, and the regulatory sequences controlling the expression of these and other trophic factors.

For example, the nucleotide sequences identified herein as encoding fish trophic factors are useful as probes for screening of libraries for the presence of related trophic factors. Libraries are constructed from cells or tissues of a desired species, such as human brain, which are then screened with all or a portion of the nucleotide sequence encoding either AF-1 or AF-2. Specific regions of interest are those portions of the nucleotide sequence which encode regions of the protein conserved between different trophic factors; between the same trophic factors from different species; and within discrete regions of the trophic factors. These regions are identified by structural analysis, using methods routinely available to those skilled in the art. These methods include electrophoretic analysis, and electron microscopy and computer assisted analysis of structure based on predicted amino acid sequence.

The amino acid sequences, and nucleotide sequences encoding the amino acid sequences, can also be used for the isolation and characterization of the regulatory sequences present in the genome which control the extent to which the neurotrophic factors are expressed in a cell, and for the screening of drugs altering expression of the trophic factors.

screening of patient samples for expression of trophic factors.

The sequences encoding the proteins disclosed herein are useful in screening of patient samples for the presence of trophic factors, using hybridization assays of patient samples, including blood and tissues. Screening can also be accomplished using antibodies, typically labelled with a fluorescent, radiolabelled, or enzymatic label, or by isolation of target cells and screening for binding activity, using methods known to those skilled in the art. Typically, one would be screening for expression on either a qualitative or quantitative basis, and for expression of functional trophic factor.

Hybridization Probes

Reaction conditions for hybridization of an oligonucleotide probe or primer to a nucleic acid sequence vary from oligonucleotide to oligonucleotide, depending on factors such as oligonucleotide length, the number of G and C nucleotides, and the composition of the buffer utilized in the hybridization reaction. Moderately stringent hybridization conditions are generally understood by those skilled in the art as conditions approximately 25° C. below the melting temperature of a perfectly base-paired double-stranded DNA. Higher specificity is generally achieved by employing incubation conditions having higher temperatures, in other words more stringent conditions. In general, the longer the sequence or higher the G and C content, the higher the temperature and/or salt concentration required. Chapter 11 of the well-known laboratory manual of Sambrook et al., Molecular Cloning: A Laboratory Manual, second edition, Cold Spring Harbor Laboratory Press, New York (1990) (which is incorporated by reference herein), describes hybridization conditions for oligonucleotide probes and primers in great detail, including a description of the factors involved and the level of stringency necessary to guarantee hybridization with specificity.

The preferred size of a hybridization probe is from 10 nucleotides to 100,000 nucleotides in length. Below 10 nucleotides, hybridized systems are not stable and will begin to denature above 20° C. Above 100,000 nucleotides, one finds that hybridization (renaturation) becomes a much slower and incomplete process, as described in greater detail in the text Molecular Genetics, Stent, G. S. and R. Calender, pp. 213–219 (1971). Ideally, the probe should be from 20 to 10,000 nucleotides. Smaller nucleotide sequences (20–100) lend themselves to production by automated organic synthetic techniques. Sequences from 100–10,000 nucleotides can be obtained from appropriate restriction endonuclease treatments. The labeling of the smaller probes with the relatively bulky chemiluminescent moieties may in some cases interfere with the hybridization process.

Production of Antibodies to AF-1 or AP-2

Animals such as mice may be immunized by administration of an amount of immunogen effective to produce an immune response. Since the proteins typically exhibit high evolutionary conservation, it may be advantageous to generate antibodies to a protein of a different species of origin than the species in which the antibodies are to be tested or utilized, looking for those antibodies which are immunoreactive with the most evolutionarily conserved regions.

The methods involved are known to those skilled in the art. For example, a mouse is subcutaneously injected in the back with 100 micrograms of antigen, followed three weeks later with an intraperitoneal injection of 100 micrograms of cocaine immunogen with adjuvant, most preferably Freund's complete adjuvant. Additional intraperitoneal injections every two weeks with adjuvant, preferably Freund's incomplete adjuvant, may be necessary until the proper titer in the mouse's blood is achieved. In order to use the mice for fusion and hybridoma production, a titer of at least 1:5000 is preferred, and a titer of 1:100,000 or more is most preferred.

In the event that the proteins are not good immunogens, they can be conjugated by methods known to those skilled in the art to suitable carriers for injection into a mammal to provoke an immune response. Preferred carriers include albumin, diphtheria toxoid and tetanus toxoid, although other suitable carriers may be readily determined by those skilled in the art.

The technique of in vitro immunization of human lymphocytes is frequently employed to generate a large variety of human monoclonal antibodies. See, e.g., T. Inai, et al., (May 1993) Histochemistry (Germany), 99(5):335–362; A. Mulder, et al., (Mar. 1993) Hum. Immunol., 36(3):186–192; H. Harada, (April 1993) et al., J. Oral Pathol. Med. (Denmark), 22(4):145–152; N. Stauber, et al., (May 26, 1993) J. Immunol. Methods (Netherlands), 161(2): 157–168; and S. Venkateswaran, et al., December 1992) Hybridoma, 11(6):729–739, which are incorporated herein by reference.

Monoclonal antibody technology can be used to obtain MAbs immunoreactive with either AF-1 or AF-2; these may be useful in purification of the trophic factors. Methods for making monoclonal antibodies are now routine for those skilled in the art. See, for example, Galfré, G. and Milstein, C., (1981) Methods Enzymol., 73:3–46, incorporated herein by reference. Briefly, hybridomas are produced using spleen cells from mice immunized with a particular trophic factor. The spleen cells of each immunized mouse is fused with mouse myeloma Sp 2/0 cells, for example, using the polyethylene glycol fusion method of Galfré,G. and Milstein, C., (1981) Methods Enzymol., 73:3–46). Growth of hybridomas, selection in HAT medium, cloning and screening of clones against antigens are carried out using standard methodology (Galfré,G. and Milstein, C., (1981) Methods Enzymol., 73:3–46).

HAT-selected clones are injected into mice to produce large quantities of MAb in ascites as described by Galfré,G. and Milstein, C., (1981) Methods Enzymol., 73:3–46, which can be purified using protein A column chromatography (BioRad, Hercules, CA). MAbs are selected on the basis of their (a) specificity for a particular protein, (b) high binding affinity, (c) isotype, and (d) stability. MAbs can be screened or tested for specificity using any of a variety of standard techniques, including Western blotting (Koren, E. et al., (1986) Biochim. Biophys. Acta 876:91–100) and enzyme-linked immunosorbent assay (ELISA) (Koren, E. et al., (1986) Biochim. Biophys. Acta 876:91–100).

Expression of Recombinant Trophic factors

Trophic factors can be obtained by isolation of naturally occurring protein as described herein. However, it is preferable to express the proteins, particularly the larger protein AF-2, by expression in a suitable recombinant host system, such as mammalian, yeast, bacteria, or insect cells. Isolation can be facilitated by making antibodies to the recombinant protein which are then immobilized on substrates for use in purification of additional trophic factors, as described above. Appropriate vectors and expression systems are commercially available, for example, from Invitrogen and Stratagene.

In some cases it may be advantageous to insert enhancers or multiple copies of the regulatory sequences or protein encoding sequences into an expression system to facilitate screening of methods and reagents for manipulation of expression and protein expression.

Screening for drugs modifying or altering the extent of trophic factor function or expression The trophic factors are useful as targets for compounds which turn on, or off, or otherwise regulate expression of these factors. The assays described above clearly provide routine methodology by which a compound can be tested for neurotrophic activity. The in vitro studies of compounds which appear to have neurotrophic activity are then confirmed by animal testing. Since the molecules are expected to be evolutionarily conserved, it is possible to conduct studies in laboratory animals such as rats to predict the effects in humans. Initial data confirms that AF-1 promotes the outgrowth of axons from rat neurons (retinal ganglion cells).

Alternatively, the assays can be based on interaction with the gene sequence encoding the trophic factor, preferably the regulatory sequences directing expression of the trophic factor. For example, antisense oligonucleotides which bind to the regulatory sequences which prevent expression of the trophic factors in fully differentiated, mature cells, can be synthesized using standard oligonucleotide synthetic chemistry. The antisense can be stabilized for pharmaceutical use using standard methodology (encapsulation in a liposome or microsphere; introduction of modified nucleotides that are resistant to degradation or groups which increase resistance to endonucleases, such as phosphorothiodates and methylation), then screened initially for alteration of trophic factor activity in transfected or naturally occurring cells which express the trophic factor, then in vivo in laboratory animals. Typically, the antisense would turn on expression by blocking those sequences which "turn off" synthesis.

Nucleic acid molecules containing the 5' regulatory sequences of the trophic factor genes can be used to regulate gene expression in vivo. Vectors, including both plasmid and eukaryotic viral vectors, may be used to express a particular recombinant 5' flanking region-gene construct in cells depending on the preference and judgment of the skilled practitioner, for example, see Sambrook et al., Chapter 16). Furthermore, a number of viral and nonviral vectors are being developed that enable the introduction of nucleic acid sequences in vivo, as described by Mulligan, (1993) *Science*, 260, 926–932; U.S. Pat. No. 4,980,286; U.S. Pat. No. 4,868,116; incorporated herein by reference. A delivery system has developed in which nucleic acid is encapsulated in cationic liposomes which can be injected intravenously or into the CNS fluid into a mammal. This system has been used to introduce DNA into the cells of multiple tissues of adult mice, including endothelium and bone marrow, as described by Zhu et al., (1993) *Science* 261, 209–211; incorporated herein by reference. Oligonucleotides can be synthesized on an automated synthesizer (e.g., Model 8700 automated synthesizer of Milligen-Biosearch, Burlington, Mass. or ABI Model 380B). In addition, antisense deoxyoligonucleotides have been shown to be effective in inhibiting gene transcription and viral replication, by Zamecnik et al., (1978) *Proc. Natl. Acad. Sci. USA* 75, 280–284; Zamecnik et al., (1986) *Proc. Natl. Acad. Sci.,* 83, 4143–4146; Wickstrom et al., (1988) *Proc. Natl. Acad. Sci. USA* 85, 1028–1032; Crooke, (1993) *FASEB J.* 7, 533–539. Recent work has shown that improved results can be obtained if the antisense oligonucleotides contain modified nucleotides, as reported by Offensperger et. al., (1993) *EMBO J.* 12, 1257–1262 (in vivo inhibition of duck hepatitis B viral replication and gene expression by antisense phosphorothioate oligodeoxynucleotides); Rosenberg et al., PCT WO 93/01286 (synthesis of sulfurthioate oligonucleotides); Agrawal et al., (1988) *Proc. Natl. Acad. Sci. USA* 85, 7079–7083 (synthesis of antisense oligonucleoside phosphoramidates and phosphorothioates to inhibit replication of human immunodeficiency virus-1); Sarin et al., (1989) *Proc. Natl. Acad. Sci. USA* 85, 7448–7794 (synthesis of antisense methylphosphonate oligonucleotides); Shaw et al., (1991) *Nucleic Acids Res* 19, 747–750 (synthesis of 3' exonuclease-resistant oligonucleotides containing 3, ' terminal phosphoroamidate modifications); incorporated herein by reference. Oligonucleotides should generally be greater than 14 nucleotides in length to ensure target sequence specificity (Maher et al., (1989); Grigoriev et al., (1992)). Many cells avidly take up oligonucleotides that are less than 50 nucleotides in length (Orson et al., (1991); Holt et al., (1988) *Mol. Cell. Biol.* 8, 963–973; Wickstrom et al., (1988) *Proc. Natl. Acad. Sci. USA* 85, 1028–1032. To reduce susceptibility to intracellular degradation, for example by 3' exonucleases, a free amine can be introduced to a 3' terminal hydroxyl group of oligonucleotides without loss of sequence binding specificity (Orson et al., 1991). Furthermore, more stable triplexes are formed if any cytosines that may be present in the oligonucleotide are methylated, and also if an intercalating agent, such as an acridine derivative, is covalently attached to a 5' terminal phosphate (via a pentamethylene bridge); again without loss of sequence specificity (Maher et al., (1989); Grigoriev et al., (1992).

Methods to produce or synthesize oligonucleotides are well known in the art. Such methods can range from standard enzymatic digestion followed by nucleotide fragment isolation, for example, as described by Sambrook et al., Chapters 5, 6, to purely synthetic methods, for example, by the cyanoethyl phosphoramidite method using a Milligen or Beckman System 1Plus DNA synthesizer (see also, Ikuta et al., in (1984) *Ann. Rev. Biochem.* 53, 323–356 (phosphotriester and phosphite-triester methods); Narang et al., in (1980) *Methods Enzymol.,* 65, 610–620 (phosphotriester method).

IV. Treatment of Nervous System Injuries and Disorders

The trophic factors can be used to stimulate nervous tissue regrowth and/or regeneration. Recent work has shown that a combination of trophic factors plus antibodies that block growth-inhibiting proteins on the surface of CNS oligodendrocytes promote increased neurite outgrowth in adult mammals (Schnell, et al., (1994) *Nature,* 367:170–173). Accordingly, AF-1 and AF-2, or their human homologues, used in conjunction with agents that prevent free radical formation, such as LaZaroid, a 21-aminosteriod, or free radical scavengers such as phenylbutylnitrone and derivatives, and counter growth-inhibiting molecules, should be of clinical significance.

Nervous System Injuries and Disorders

Nerve cells, or neurons, typically consist of a cell body, which contains the nucleus and most of the organelles; multiple dendrites, the processes that receive stimuli; and an axon, a process that generates or conducts nerve impulses to other cells, such as muscle, gland, and other neurons. Nerve fibers are axons wrapped in special cellular sheaths. Groups of nerve fibers make up the tracts of the brain, spinal cord, and peripheral nerves. The sheath cell of most axons in adult nerve tissue is the Schwann cell in peripheral nerves and the oligodendrocyte in central nerve fibers. Small diameter axons usually have no sheath and are referred to as unmyelinated nerve fibers. Thicker axons wrapped in cellular sheaths are called myelinated nerve fibers. In the peripheral nervous system, the nerve fibers are grouped into bundles and form the nerves. Most peripheral nerves contain myelinated fibers.

Nerve processes in the central nervous system (brain and spinal cord) may regenerate within narrow limits through synthetic activity of the cell body, as long as it remains alive. However, a significant problem is that the processes usually cannot regenerate fast enough to avoid blockage by astroglial scar tissue. Thus regeneration may be blocked by a physical barrier before regeneration can occur. Processes in the peripheral nervous system may also regenerate, as long as the cell body lives. The degenerative and regenerative steps have been described but are not well understood. When a peripheral nerve is severed, the axon segments proximal to the cut grow in the direction of the myelin sheaths that previously housed the axon segments distal to the cut. Only the axons that successfully match the sheaths will regenerate and reach the effector cells. Thus, growth of processes that occurs before scar tissue formation results in more successful regeneration.

Axonal degeneration or loss of axons is most common in toxic, inherited, traumatic, and ischemic diseases. It may occur in concert with demyelinating diseases, that in turn may be inherited or autoimmune inflammatory disorders. A mixed picture of degeneration and demyelination, resulting in axonal loss, occurs, for example in diabetes mellitus.

Damage to nerve processes, especially axons, from trauma may occur in the central and peripheral nervous systems, including brain, cranial nerves, spinal cord, and peripheral nerves. Types of damage caused by trauma include damage caused by direct cuts, swelling and compression, bruising, and the like, all of which may result in loss of all of part of the affected axons. Trauma may also create entry pathways for microorganisms and air or cut off the blood supply to nerves. The effector cells whose function is disrupted by destruction of nerve axons include skeletal muscle; smooth muscle of the blood and lymph vessels; smooth muscle of the major organ systems, including the respiratory, genito-urinary, and digestive systems; gland cells of the endocrine and exocrine glands; and other nerve cells. Thus, the physiologic function of virtually any system in the body may be altered by injury to the nerve supply that involves loss of axons.

An example of traumatic injury is the severance of a motor nerve to a skeletal muscle. The axons distal to the cut degenerate over a period of days. The muscle fibers that are disconnected from the nervous system undergo fasciculations, and later a profound denervation atrophy, depending on whether other innervation exists. Such muscle becomes non-functional unless regeneration of its innervation occurs.

Demyelinating diseases also are associated with loss of axons. These diseases may be caused by autoimmunity and/or viral infection and genetically determined defects, and include multiple sclerosis, acute disseminated encephalomyelitis, and acute necrotizing hemorrhagic encephalomyelitis. Demyelination and loss of axons may also be due to toxins such as carbon monoxide.

Axons may be lost also through degenerative diseases of the nervous system, for example, in amyotrophic lateral sclerosis and progressive spinal muscular atrophy; in some motor neuropathies; in acute, chronic demyelinating, and other types of polyneuropathies caused, for example, by massive intoxication or arsenic, viral infections (Guillain-Barre syndrome, herpes, cytomegalovirus, Epstein-Barr), surgical trauma, lymphoma, lupus, diabetes, dysproteinemia, and cold injury.

Regeneration after axonal degeneration may take from two months to more than a year, depending on the severity and distance to be covered.

Pharmaceutical Compositions

The proteins can be administered as a pharmaceutically acceptable acid- or base- addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The trophic factors can be modified to increase in vivo half-life, by chemical modification of the amino acids or by attachment to a carrier molecule or inert substrate. For example, the peptides can be conjugated to a carrier protein such as keyhole limpet hemocyanin by its N-terminal cysteine by standard procedures such as the commercial Imject kit from Pierce Chemicals or expressed as a fusion protein, which may have increased efficacy and half-life in vivo.

Peptides containing cyclopropyl amino acids, or amino acids derivatized in a similar fashion, can also be used. These peptides retain their original activity but have increased half-lives in vivo. Methods for modifying amino acids, and their use, are known to those skilled in the art, for example, as described in U.S. Pat. No. 4,629,784 to Stammer.

Administration to a Patient

Based on the in vitro studies, the $IC_{50}$, the dose of a trophic factor required to effect, or enhance, neuronal growth, usually fall in the picomolar. This dosage will be dependent, in part, on whether one or more proteins are administered.

Trophic factors are preferably administered in a pharmaceutically acceptable vehicle. Suitable pharmaceutical vehicles are known to those skilled in the art. For example, the compound will usually be dissolved or suspended in sterile water or saline. The compounds can also be administered locally by topical application of a solution.

Alternatively, the compound may be administered in liposomes or microspheres (or microparticles). Methods for preparing liposomes and microspheres for administration to a patient are known to those skilled in the art.

U.S. Pat. No. 4,789,734 describe methods for encapsulating biological materials in liposomes. Essentially, the material is dissolved in an aqueous solution, the appropriate phospholipids and lipids added, along with surfactants if required, and the material dialyzed or sonicated, as necessary. A review of known methods is by G. Gregoriadis, Chapter 14. "Liposomes", *Drug Carriers in Biology and Medicine* pp. 287–341 (Academic Press, 1979).

Microspheres formed of polymers or proteins are well known to those skilled in the art. The microspheres, or composite of microspheres, are implanted for slow release over a period of time, ranging from days to months. See, for example, U.S. Pat. Nos. 4,906,474, 4,925,673, and 3,625,214.

The polymeric devices are preferably manufactured using a method that evenly disperses the anesthetic throughout the device, such as solvent casting, spray drying or hot melt, or by compression molding. Devices can be shaped as slabs, beads, pellets, microparticles, including microspheres and microcapsules, or formed into a paste. Microparticles, microspheres, and microcapsules are collectively referred to herein as "microparticles". The device can be coated with another polymer or other material to alter release characteristics or enhance biocompatibility. The microparticles can be administered as a suspension or as a device within a gelatin capsule, or used to form a paste, for example.

In the preferred embodiments, the device will be in the form of microparticles. A desired release profile can be achieved by using a mixture of microparticles formed of polymers having different release rates, for example, polymers releasing in one day, three days, and one week, so that linear release is achieved even when each polymer per se does not release linearly over the same time period.

In the preferred method of administration of the liposomes, microparticles or slabs, the devices are administered by injection at the site where the effect is to be achieved. Alternatively, the device is surgically implanted at the site. Implantation of devices can be accomplished in clinical practice either through a surgical field or via needles.

Controlled release can also be achieved by continuous infusion via a minipump, for example, of the type used to delivery pain medication via an epidural.

The present invention will be further understood by reference to the following non-limiting examples.

EXAMPLE 1

Development of Model to identify endogenous neurotrophic factors

An experimental model in which one could identify endogenous factors that induce regeneration of the optic nerve was developed. The goal was to establish a cell culture system enriched in retinal ganglion cells maintained at low cell densities to allow for objective quantitation of neurite outgrowth and to minimize indirect effects mediated through other cell types; moreover, it was important to use retinas from 'naive' animals cultured in the absence of serum to identify the factors that initiate outgrowth.

The results demonstrate that dissociated retinal ganglion cells survive well in the defined, serum-free conditions established here, but show little axonal outgrowth unless exposed to one of two factors that are secreted by the glial cells of the goldfish optic nerve. These factors are (a) a protease-sensitive, heat-resistant molecule that appears to be less than one kilodalton in size, and (b) a heat-and protease-sensitive molecule of 8 to 15 kDa. Retrograde labeling experiments demonstrate that the retinal ganglion cells are the principal targets of these factors, reinforcing the likelihood that these molecules play a major role in initiating optic nerve regeneration in vivo.

Methods.

Conditioned Media.

Comet goldfish (3 to 4 inches in length, Mt. Parnell Fisheries, Ft. Loudon, Pa.) were used to prepare both conditioned medium (CM) and dissociated retinal cultures. Animals were anesthetized by chilling to 4° C. and then sacrificed by cervical transection. Optic nerves (ONs) and tracts were dissected free of bone and connective tissue in two stages: a gross dissection under 2× magnification to yield optic nerves and tracts freed from the eyes and optic tecta but with some connective tissue and bone still attached, then a second stage carried out under 12× magnification using a table-top dissecting microscope (Wild). Following procedures described by Schwartz, et al. (1985) and modified by Finkelstein, et al. (1987), 6 ONs were placed in 3 ml HEPES-buffered Liebovitz L-15 medium (Gibco/BRL, Gaithersburg, Md.) and cut into 1 to 2 mm segments. These were incubated for 3 to 4 hrs at 37° C. in a 5% $CO_2$ environment, then filter-sterilized with a 0.2 $\mu$m pore low protein-binding syringe filter (Acrodisc, Gelman Sciences, Ann Arbor, Mich.). CM was usually aliquoted and stored at −80° C. immediately after preparation, though in some cases it was stored at 4° C. for one to five days before being fractionated or used in bioassays. Protein determinations (Bradford kit, BSA standard; BioRad, Richmond, Calif.) carried out on several batches of CM showed a protein concentration of about 100 $\mu$g/ml.

In cases where optic nerve surgery was carried out prior to dissection, animals were anesthetized in 0.5 mg/ml 3-aminobenzoic acid ethylester (Sigma Chemical Co., St. Louis, Mo.) and placed in a Plexiglass™ holder which fixed the position of the head and delivered a constant flow of aerated tank water to the gills. Two incisions were made in the superior rim of the orbit 3 mm apart, the bone flap was retracted, and orbital soft tissue and adventitia were dissected away to expose the optic nerves. Nerves were crushed bilaterally 1 to 2 mm behind the eyes using curved 4' jeweler's forceps. Orbital bleeding or transection of the nerves were considered grounds for eliminating animals from the study.

Dissociated Retinal Cultures.

Cultures were prepared using a modification of techniques described by Landreth & Agranoff (1976, 1979) and Dowling, et al. (1985) Brain Res., 360:331–338. Goldfish were dark-adapted in covered tanks for at least 30 min before being sacrificed. Eyes were removed rapidly and washed in sterile L-15, 70% ethanol, and L-15 in quick succession. Lens, cornea, and iris were removed using iris scissors. The retina was teased from the sclera and pigment epithelium using microdissection scissors and jeweler's forceps under 25× magnification. Four retinas were placed in 5 ml of sterile digestion solution inside a laminar flow hood, in which the remainder of the culture preparation was carried out. To prepare the digestion solution, 100 units of papain (Worthington) plus 2.5 mg L-cysteine (Sigma) were added to 5 ml HEPES buffered L-15 brought to pH 7.4 with NaOH, then filter sterilized. After 45 min, the digestion solution was replaced with 5 ml sterile L-15 and the tissue was gently triturated 5 times to break the retina into small pieces. The solution was again replaced with 5 ml sterile L-15 and the tissue was triturated vigorously 5 times, separating retinas into fine fragments and removing photoreceptor cells. This step was repeated in fresh L-15 to create a single cell suspension. Successive trituration steps enriched the concentration of ganglion cells by removing most of the photoreceptor cells and mesenchymal tissue.

Cells were plated in 24-well tissue culture dishes (Costar, Cambridge, Mass.) coated with poly-L-lysine (MW greater 300,000, Sigma). Each well first received 200 $\mu$l of 2× medium E, which was developed based upon publications of Bottenstein (1983) In: Current Methods in Cellular Neurobiology, Vol. IV: Model Systems. J. L. Barker and J. F. McKelvy, eds., 107–130 (John Wiley & Sons, New York); Dichter Brain. Res., 149:279–293 (1978); Walicke, et al. J. Neurosci., 6:114–121 (1986); and Aizenman & deVellis Brain Res., 406:32–42 (1987)). At final concentration, Medium E contains 20 nM hydrocortisone, 1 mM kainurinate, 100 μM putrescine, 20 nM progesterone, 30 nM selenium, 0.3 nM 3, 3'5-triiodo-L-thyronine, 50 μg/ml transferrin, 150 U/ml catalase, 60 U/ml superoxide dismutase, 1% bovine serum albumin (Type V), 10 μg/ml gentamicin, 5 μg/ml insulin, and 15 mM HEPES (all reagents from Sigma). Medium E was titrated to pH 7.4 and filter-sterilized prior to being added to culture plates. To facilitate preparation and to help ensure reproducibility, the first six constituents were prepared together and stored at a 25× concentration in 0.5 ml aliquots at -20° C. After adding Medium E, each well received 50 μl of cell suspension, then the experimental or control sample brought up to 150 μl with L-15. Except where noted otherwise, experimental samples were set up in a blinded, randomized fashion by another member of the lab so that the investigator was unaware of the conditions present in any well. Within a given experiment, each experimental condition was represented in 4 to 8 wells; every experiment also included at least 4 wells of a positive control (of previously validated CM at a 5 to 15% concentration) and at least 4 wells of an L-15 and Medium E alone as a negative control. Plates were incubated for 5 to 6 days in a dark humidified tank at room temperature before being evaluated. Most experiments were repeated with material from 2 to 5 separate preparations. Data are presented as the mean ± standard error for the 4 to 8 replicates. Where noted, some results are normalized by subtracting the growth in the negative controls and then dividing by the net growth in the positive controls.

Neurite Outgrowth Assay.

Neurite outgrowth was quantified after 5 or 6 days. Culture medium was replaced by 0.1 mg/ml 5,6-carboxyfluorescein diacetate (CFDA: Sigma) in phosphate-buffered saline (PBS) and incubated at room temperature for 10 min. CFDA, a vital dye, is taken up and metabolized by living cells to yield a fluorescent product that is distributed throughout the entire cell, allowing us to assess both cell viability and neurite outgrowth. Cultures were examined at 100×magnification under fluorescent illumination (Nikon AF-BS inverted microscope) using a green barrier filter. The total number of viable cells in fourteen consecutive microscope frames (i.e., a single well radius) were recorded starting at the top of the well. Cells matching the morphological criteria for retinal ganglion cells (RGCs), as established in retrograde labeling experiments (i.e., size and number of processes), were scored according to the length of their neurites, i.e., cells with neurites extending one to five cell diameters in length, five to ten cell diameters, 10 to 20 cell diameter, and greater than 20 cell diameter. In most instances, however, the last three bins were collapsed to give a single measure of neurite outgrowth, i.e., ([number of cells with neurites greater than five cell diameters]+[total number of viable cells]×100).

Identification of Retinal Ganglion Cells.

Fish were anesthetized and a series of scalpel incisions were made within a region of the skull defined by the bone sutures above the optic tectum. The bone flap was retracted and crystals of the lipophilic dye, 4-(4-didecylaminostyryl)-N-methylpyridinium iodide (4-di 10 ASP: Molecular Probes, Inc., Portland, Oreg.) were placed directly on the optic tecta. The bone flap was replaced and sealed with Aron Alpha (Ted Pella, Inc.). After allowing five to nine days for the dye to be transported back to the ganglion cells, retinas were dissected and cultured in the presence of either 10% CM or control media alone, as described above. After six days in culture, neurite outgrowth was quantified under fluorescent microscopy for cells that were retrogradely labeled with 4-di-10 ASP. In addition to providing information about neurite outgrowth in ganglion cells per se, these studies helped establish criteria that were used to identify RGCs in the standard heterogeneous cultures.

EXAMPLES2

Determination of source of tropic factors

Source of Trophic Factors.

To investigate whether the trophic factors are actively secreted or just released from cells of the optic nerve that are damaged during the dissection, the activity of the high- and low-molecular weight fractions of CM and optic nerve cytosol were compared. Cytosol fractions were prepared by homogenizing 10 optic nerves in 25 mM HEPES, pH 7.4 or L-15. The high-speed supernatant of this extract was matched for protein concentration to whole CM using the BioRad™ protein assay. The optic nerve cytosol and CM were then separated into high and low molecular weight fractions with a Centriprep-3™ filter. Fractions were screened in the bioassay. The factors were also examined to determine if they were secreted selectively by the optic nerve by comparing standard CM with media conditioned with factors secreted by other goldfish tissues. The optic nerves required to prepare 3 ml of CM were weighed prior to mincing. Equal masses of tissue from goldfish skeletal muscle, liver, and gill were used to prepare conditioned media as described above.

To evaluate the effects of molecules previously found to affect growth in retinal explant cultures, taurine, at concentrations of $10^{-9}$ to $10^{-3}$M (Sigma), retinoic acid ($10^{-9}$ to $10^{-4}$M: Sigma), and NGF (β-subunit, 100 nM: Collaborative Research, Bedford, Mass.) were tested in the bioassay. Additional experiments were carried out to examine whether the response of RGCs to CM depended on the density of plating in culture. In addition to the standard cell density used throughout the studies, the cells were also plated at ⅓, ⅑ and 1/27 of this density. Finally, experiments were carried out to compare the axonal outgrowth of 'primed' retinal ganglion cells, which had begun to regenerate their axons in vivo, with that of naive retinas dissected from previously intact fish. Retinas were primed by allowing the regenerative process to proceed in vivo for 10 days prior to dissociating and plating, a period previously shown to maximally enhance axonal outgrowth in retinal explants (Landreth & Agranoff, 1976), and in nerves crushed a second time and allowed to regenerate in vivo (McQuarrie and Grafstein, (1981) *Brain Research,* 216:253–264). Comparisons made between conditions are based on 2-tailed t-tests throughout.

Results.

Dissociated retinal cells respond to factors derived from the optic nerve.

The response of dissociated retinal cells to factors secreted by the optic nerve was determined using the dye 5,6-CFDA. Under baseline conditions, cells remain viable but show little outgrowth. With the addition of CM containing factors secreted by the optic nerve, cells 10–17 μm across extend one or two long processes of a uniformly thin caliber, which sometime terminate in a prominent growth cone. Larger, polygonal cells are not counted in quantifying neurite outgrowth.

Six days after plating with L-15 and medium E alone, retinal cells remained viable but showed little outgrowth. Staining with 5,6-CFDA revealed a density of about 70 cells/mm². Counting 14 microscope fields (i.e., 1 well radius) allowed a sampling of 200–300 cells/well. Addition of media conditioned by factors secreted by the optic nerve induced cells to extend long neurites that resemble axons.

Dose-response Characteristics.

Figure 1C:
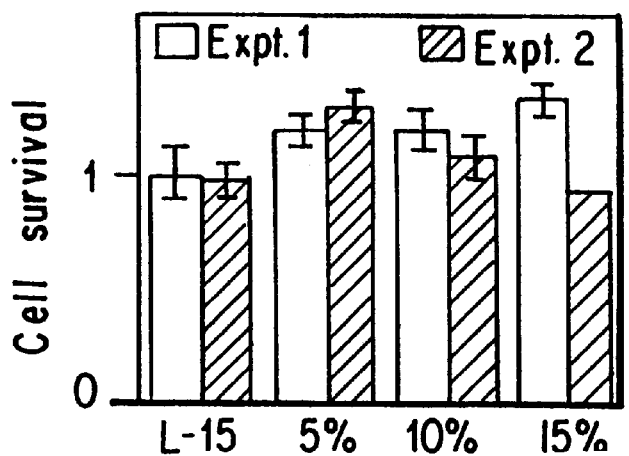
FIG. 1c is a graph of cell survival as a function of CM concentration in two independent experiments (5,6-CFDA labeled cells counted in 14 successive microscope fields, averaged for 4 wells, normalized by L-15 control values).

The response of retinal cells to increasing concentrations of CM is shown in FIGS. 1A1, 1A2, 1A3 and FIG. 1A4 are histograms of axon length distribution 5 days after being cultured with CM at the indicated concentrations. Although the number of cells extending processes 1 to 5 cell diameter in length changes little with increasing concentrations of CM, the number extending processes greater than 5 cell diameter in length increases greatly. FIG. 1b are dose-response curves of two separate experiments showing neurite outgrowth in response to increasing concentrations of CM. Data represent the percentage of cells with processes greater than 5 cell diameter in length, a cut-off point selected based upon the histogram date in FIGS. 1A1, 1A2, 1A3 and 1A4. In both experiments as shown in FIG. 1A1, maximal outgrowth is attached in response to CM at a 10% concentration (i.e., total protein concentration of about 10 $\mu$g/ml). FIG. 1c is a graph of cell survival as a function of CM concentration in two independent experiments.

Figure 4:
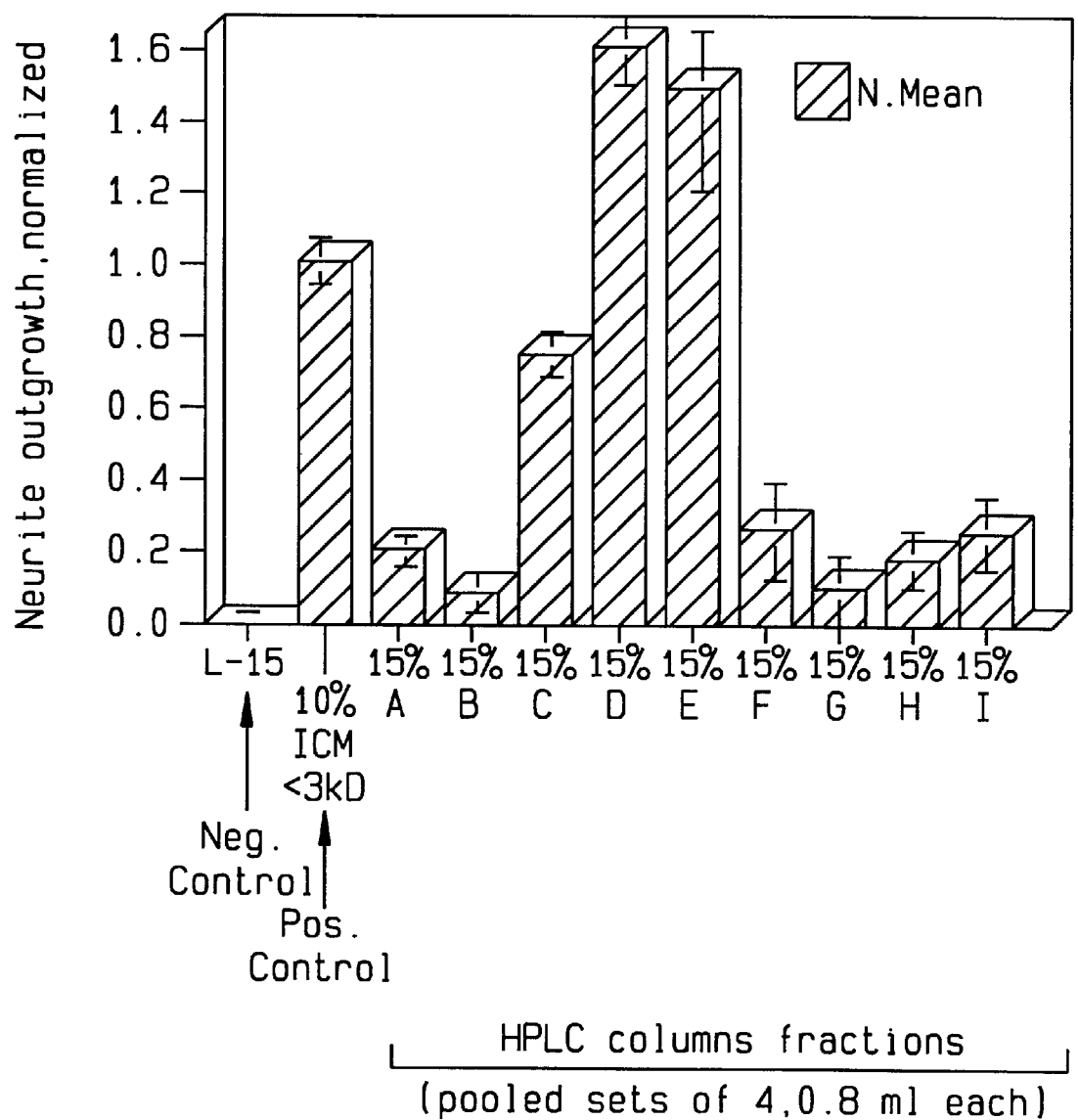

As indicated in the histograms of FIG. 1A1, in the absence of CM, 4% of cells had neurites in the range of 1 to 5 cell diameters and fewer than 1% had processes any longer than this. With the addition of CM at a 5% concentration, as shown in FIG. 1A2, the process length distribution shifted markedly: 7% of cells now had neurites 5 to 10 cells in length and 2% had even longer processes. With higher concentrations of CM (15%), as shown in FIG. 1A4, there were few cells left with axons in the 1 to 5 cell diameter. As in all subsequent experiments, the results shown are the means of greater than or equal to 4 wells for each sample ±S.E.M. On the basis of the distribution patterns found here, most subsequent results have been represented as the percentage of cells with axons greater than 5 cell diameters, a cut-off point which discriminates responsive and non-responsive groups well.

FIG. 1b shows the dose-response curves of two consecutive experiments using different preparations of CM and retinas. For CM concentrations up to 10%, the number of cells with axons greater than 5 cell diameters in length increases, then levels off (outgrowth in response to 5% CM vs. L-15 ±Medium E alone, $p<0.001$ for both experiments; growth with 10% CM vs. 5% CM, $p<0.02$ for both; error bars not shown if less than 1%; one of these 2 experiments was carried out early in the study and was not blinded). The maximum number of cells responding differs somewhat between the two experiments, perhaps reflecting differences in the percentage of RGCs in the two preparations. The inset demonstrates that CM has little effect on cell viability. These data, taken from two studies, show the number of viable cells counted in 14 consecutive microscope fields (i.e., 1 well diameter), averaged over 4 wells for each condition, at increasing concentrations of CM. Data are normalized by the number of viable cells in the negative control (to account for differences in plating densities in the two experiments). Although viability appeared to be elevated in response to 15% CM in one experiment, this failed to achieve statistical significance (15% CM vs. L-15, $p=0.21$), and was not seen in the other experiment.

Identification of Retinal Ganglion Cells.

Retrograde labeling was used to investigate outgrowth in retinal ganglion cells per se. Application of 4-Di-10 ASP to a small region of the optic tectum resulted in the retrograde labeling of 4–5% of the viable cells in culture. These cells were ellipsoid, measuring 8–10×16–18 $\mu$m, similar to the dimensions of RGCs reported by Schwartz & Agranoff (1981) *Brain Res.*, 206:331–343. The cells labeled with 4-di-10 ASP showed little spontaneous outgrowth in the presence of L-15 and Medium E alone; in response to 10% CM, however, these cells showed twice the level of neurite outgrowth observed in the overall cell population. The survival of RGCs is unaffected by CM. For both sets of retinas, the number of retrogradely labeled cells in culture, divided by the total number of viable cells, was 4 to 5% irrespective of the presence or absence of CM. For outgrowth in RGCs vs. total cells, $p<0.005$ for both sets of retinas.

Retinal ganglion cells were labeled by applying the lipophilic dye 4-di-10 ASP to the optic tectum 7 days prior to culturing. After 6 days in culture, labeled cells extended one or two processes in response to CM. These cells generally formed one or two long, thin processes. For both sets of retinas, the viability of retrogradely labeled cells relative to the overall cell population showed no change with the addition of CM. Thus, CM stimulates neurite outgrowth from RGCs selectively, and this effect is not a consequence of enhancing the survival of this cell type. This study also provides criteria (diameter, number of processes) for distinguishing the ganglion cells in the mixed, 5,6-CFDA-stained cultures. In the mixed cultures, neurite outgrowth is counted only from cells that match the criteria for RGCs and find that 15%–25% of the total population extends neurites greater than 5 cell diameter. Since it can be determined from the retrograde labeling study that approximately one-third of neurons identified as RGCs are growing vigorously under these conditions, it follows that RGCs constitute 45–75% of the cells in the mixed cultures.

Tissue Specificity of Conditioned Media.

Unlike media conditioned by the goldfish optic nerve, media conditioned by an equal mass of goldfish skeletal muscle, gill, or liver showed little neurite-promoting activity (all samples differ from optic nerve CM at $p<0.01$; experiment not blinded).

EXAMPLE 3

Isolation and characterization of neurotropic factors optic Nerve CM Contains Two Trophic Factors.

Preliminary separations carried out by ultrafiltration showed that all of the trophic activity passed through ultrafiltration devices with molecular weight cut-offs of 100 and 1000 kDa; in addition, a great deal of the activity passed through filters with cut-offs of 10,000 and 3,000 Da. On a size-exclusion column with a molecular weight cut-off of 6 kDa (i.e., a desalting column: Bio-Rad), neurite-promoting activity was found to be present both in fractions containing protein (as assessed by spectroscopy at $O.D._{280}$) and in low-molecular weight fractions (containing salts, as assessed by measuring conductivity). On the basis of these observations, conditioned media was prepared from optic nerves dissected either from normal goldfish or from animals 3 or 7 days after bilateral optic nerve crush, then used ultrafiltration to separate the CM samples into fractions less than 3,000 Da and greater than 3,000 Da in size. CM obtained from either intact or injured optic nerves yielded both high and low molecular weight neurite-promoting factors (all samples show higher growth than the L-15 control at a level of $p<0.002$). To simplify the figure, data have been represented by first subtracting the level of growth in negative controls grown with Medium E and L-15 alone (3±0.2% [mean±S.E.M.] experiment), particular experiment), then normalizing by the net growth in positive controls treated with unfractionated CM (21.3±2.3% in this instance). The data in FIG. 2a suggest that most of the activity in unfractionated CM can be attributed to the smaller factor, though this is less evident in the material collected at three days post-injury. Qualitatively, the presence of high- and low-molecular weight trophic factors has been observed repeatedly in CM prepared from either intact or injured optic nerves.

Size Fractionation.

Figure 2A:
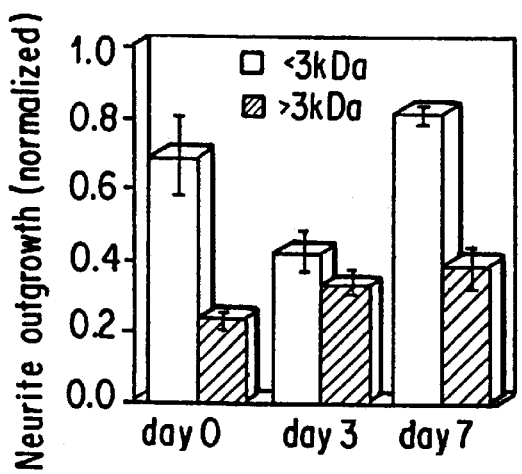
FIGS. 2a and 2b are graphs of neurite-promoting activity versus size fractions of CM.

Several methods were used to determine the size of the active factors. CM was first separated by centrifugal ultrafiltration using filters with molecular weight cut-offs of 10, 100, and 1000 kDa (Amicon, Beverly, Mass.). Filtrates and retentates were tested in the bioassay. Next, CM was passed through a 6 kDa desalting column (BioRad) and fractions were monitored by absorbance at 280 nm (for protein) and by measuring conductivity (for low-molecular weight fractions containing salts). Fractions containing high and low molecular weight constituents were evaluated by bioassay and were both found to be active, as shown in FIG. 2a. Fractions greater than 6 kDa were pooled and concentrated 10- to 100-fold using a Centriprep-3™ filter (Amicon) with a 3 kDa cut-off. This material was then separated by high performance liquid chromatography (HPLC, Beckman Instruments) using a Biosep Sec™-S3000 N-capped bonded silica column (Phenomenex, Torrance, Calif.). Column fractions were screened in the bioassay, as shown in FIG. 2c. The low molecular weight material (less than 6 kDa) was characterized further by being passed through a Centriprep-3™ filter (Amicon) or a Microsep™ (Filtron, Northborough, Mass.) centrifugal filter with a 1 kDa cut-off.

Heat and Protease Treatment.

To determine whether neurite-promoting factors in CM are polypeptides, high and low molecular weight fractions were heated to 95° C. for 15 min or exposed to 0.1% trypsin. Soybean trypsin inhibitor at 0.125% was added either together with the trypsin or after 1 or 2 hr incubation with trypsin. Samples were then screened in the bioassay. In addition, the less than 3 kDa fraction was exposed to pronase (Sigma) at 10 U/ml for 8 h (49° C.), or to proteinase K (PK, Boehringer Mannheim, Indianapolis, Ind.: 50 $\mu$g/ml, 56° C., 1 h). Following incubation, the enzymes were separated from low molecular weight components using a Centriprep-3™ filter and the filtrates were bioassayed. Controls included heating active fractions without enzymes to verify that heat per se did not cause inactivation; and incubating the enzymes by themselves at 56° for 1 h, filtering, then adding the filtrate to the less than 3 kDa fraction to verify that the proteases were not generating autolytic fragments that might affect cell growth.

Sensitivity of the two factors to heat and proteases indicated that both factors are polypeptides. After heating at 95° C. for 15 min, unfractionated CM (5%) lost half of its activity; the high molecular weight fraction, by itself (at a 20% concentration), lost nearly all of its activity. The low molecular weight factor by itself, treated for 1 h at 56° C. or for 15 min at 95° C., lost only 30% of its activity.

Exposure to trypsin for 1 or 2 h diminished the activity of unfractionated CM by about 60%, although the low molecular weight fraction by itself showed little loss in activity after trypsin digestion. In the control, soybean trypsin inhibitor added at the same time as trypsin prevented the loss of activity. The sensitivity of the low molecular weight factor to proteases was examined further by treating it with pronase (8 h, 40° C.) or with proteinase K (1 h, 56° C.). Following the incubations, low molecular weight components were separated from the enzymes by ultrafiltration and then tested in the bioassay. Controls were incubated without the enzymes present.

Pronase, like trypsin, had little effect on the activity of the low molecular weight factor(s). Proteinase K, however, diminished its activity by 80% (treatment at 56° C. with and without proteinase K significant at p=0.004). Thus, both the large and the small factors appear to be polypeptides.

Anion Exchange Chromatography.

Anion-exchange chromatography was carried out on diethylaminoethyl cellulose columns (DE-52, Whatman, Hillsboro, Oreg.). DE-52 beads were equilibrated with 25 mM HEPES at pH 8.4, then added at a ratio of 0.5 ml hydrated beads: 10 ml CM (which had been desalted using a 6 kDa cut-off size-exclusion column). After an overnight incubation (4° C.), the mixture was pipetted into a 5 mm I.D., glass Econo-column (BioRad). The unbound fraction and the first rinse of the column with 25 mM HEPES were pooled. Bound proteins were then eluted with successive 3 ml steps of 0.1, 0.2, 0.5 and 1.0M NaCl in 25 mM HEPES. Fractions were divided into aliquots and stored at -80° C. for bioassays. Ion-exchange chromatography was also carried out on the high molecular weight fraction of CM at pH 10.

The Smaller Trophic Factor Passes Through a 1,000Da Filter.

Figure 2B:
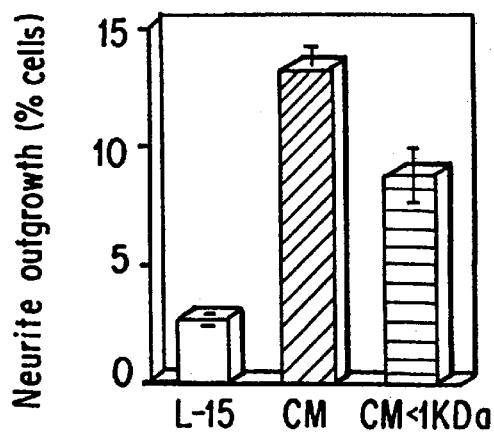
Figure 2C:
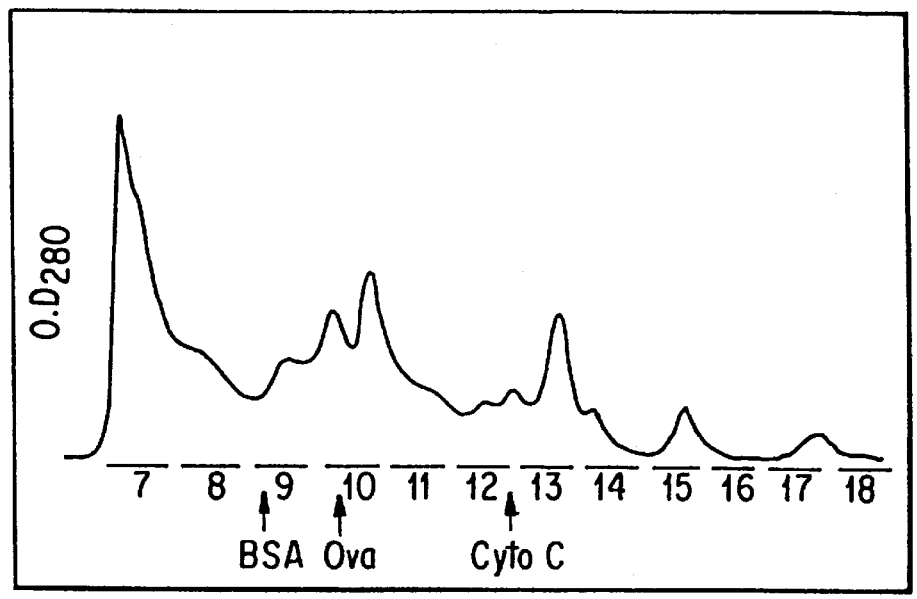
FIG. 2c is a chromatogram of the high molecular weight fraction of CM separated by size-exclusion high performance liquid chromatography (optical density, O.D., read at 280 nm). The high molecular weight fraction was concentrated 70-fold and then separated into 1 ml fractions (numbered bars). Arrows indicate the retention times of the molecular weight calibration standards (BSA, bovine serum albumin; Ova, ovalbumin; Cyto C, cytochrome C).

Further fractionation of CM using a Microsep™ filter with a 1,000 Da cut-off yields a high level of activity in the filtrate, as shown by FIG. 2b; less than 1,000 Da fraction versus L-15 control, P=0.01; less than 1,000 Da fraction versus total CM, P=0.06. Since the ability of a molecule to pass through this pore size depends on its shape as well as its size, however, this is not absolutely determined of size.

Size Estimate of the Larger Trophic Factor.

Figure 2D:
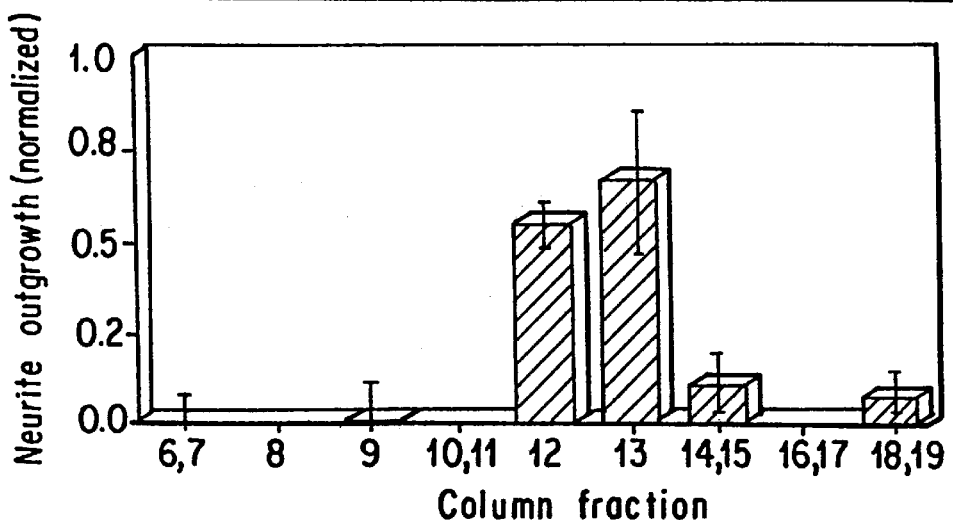
FIG. 2d is a graph of neurite outgrowth in response to column fractions assayed at concentrations of 25% (calculated on the basis of the starting material). Fractions were first bioassayed in pairs; if any activity was seen, they were retested individually, otherwise they were retested in pairs. Only fractions 12 and 13 contained significant neurite-promoting activity.
Figure 3:
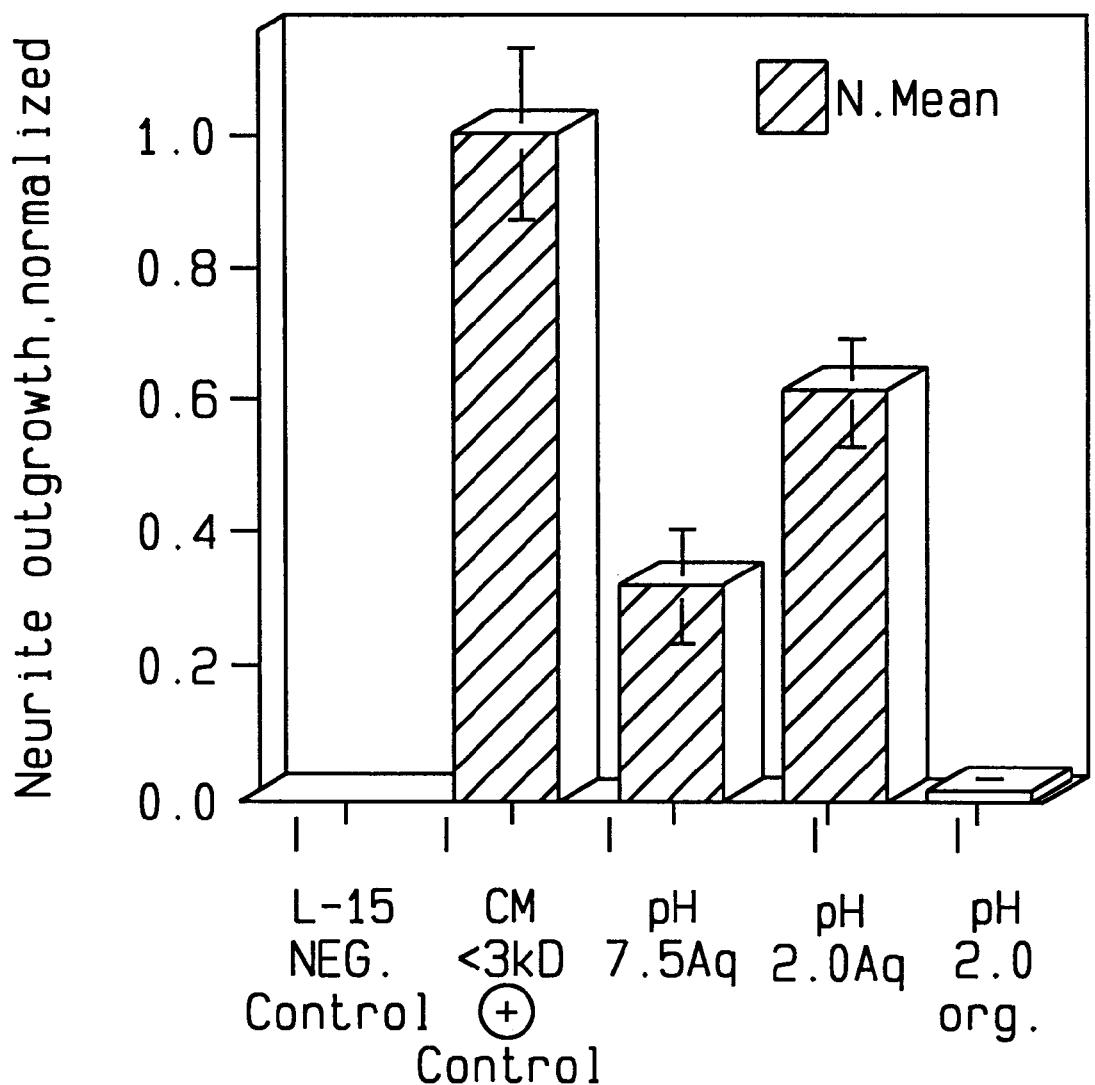

FIG. 2c shows the elution profile of the high molecular weight fraction of CM when separated by size-exclusion HPLC. As seen by SDS-polyacrylamide gel electrophoresis (Caday, et al., 1989) and the present chromatogram, CM contains a complex mixture of proteins. Fractions were initially bioassayed in groups of two; if pooled fractions showed any activity, they were rescreened individually, or in pairs again if not. High levels of activity were observed in fractions 12 and 13 in both the initial and in the secondary screens (FIG. 2d; fraction 12 vs. L-15, P=0.01; fraction 13 vs. L-15, P=0.053; all others N.S.). The active factor has a similar retention time as cytochrome C (12 kDa; FIG. 2d), so the size is estimated to be in the range of between 8,000 and 15,000 Da.

In some experiments, an additional peak of activity has been observed at 70,000 to 100,000 Da, but this has not been reproducible. This larger molecule may be unstable and degrade to form the 12,000 Da factor, or it may be a multimeric complex that dissociates under certain experimental conditions.

Charge and substrate Binding.

Ion-exchange chromatography was used to purify the larger factor further. Separation of the high molecular weight component of CM by DEAE-anion-exchange chromatography was performed. At pH 8.4, neurite-promoting activity was recovered in the unbound fraction, whereas at pH 10, the active factor bound to the column and eluted with 0.2M NaCl. Neither component of CM acts as a substrate-bound trophic factor. CM was separated into high and low molecular weight fractions by ultrafiltration (3,000 Da cut-off). Prolonged exposure of the larger protein to elevated pH appears to reduce its activity significantly.

Polylysine-coated plates were incubated overnight with either the high or low molecular weight fractions of CM, either at full-strength or at a 1:10 dilution. After rinsing wells to remove unbound material, no neurite-promoting activity was retained after rinsing plates with L-15. Thus, neither the large nor the small factor acts as a substrate-bound growth factor.

FIG. 4 is a graph of neurite outgrowth showing that when the partially purified extract containing the low molecular weight trophic factor, AF-1, is separated by reversed phase HPLC, the active component appears in the column fractions designated FC, FD, and FE. As described above, the negative control (L-15) is the tissue culture medium alone; the positive control is the unfractionated low molecular weight component of the molecules secreted by optic nerve glia (1CM less than 3,000 Da, 10% concentration); FA-FI indicate column fractions from the high performance liquid chromatography separation.

Intra- and Extracellular Concentration of the Two Factors.

Whether the two neurite-promoting factors are actively secreted was then determined by comparing their activity in CM and in the high-speed supernatant fraction of optic nerve homogenates. Samples were used in the bioassay at concentrations of 10% and 20%, adjusting the protein concentration of the optic nerve cytosol to match that of the CM (i.e., a 10% concentration is equivalent to a protein concentration prior to ultrafiltration of about 10 μg/ml protein for each. This is based on the hypothesis that most of the proteins found in CM arise from cell lysis and not by active secretion).

The low molecular weight factor is considerably more concentrated in CM than in the ON Cyto (P=0.002). These data, which have been replicated in two more experiments, suggest that the smaller molecule is actively secreted. The larger factor is present at equal concentrations intra- and extracellularly.

Effect of Cell Density.

To determine whether cell density affects the response of retinal ganglion cells to CM, retinas were plated at either the standard density used throughout these studies (about 70 cells/mm$^2$) or at increasingly lower densities. If RGCs are responding to a secondary factor released by another type of cell which is the direct target of CM, then as the number of these other cells decrease and the concentration of a secondary factor decreases, one would expect to find a diminished response of RGCs at lower cell densities. At one-third the standard cell density (about 25 cells/mm$^2$), retinal neurons appeared to have a slightly higher response to CM than at the standard density (N.S.), and with another 3-fold dilution, outgrowth was only 30% lower than at the normal plating density [P=0.18, not significant]. At 1/27 the standard density, outgrowth did show a significant decrease (P=0.05).

Absence of a Priming Effect.

Retinas dissected from either previously intact fish or fish which had undergone optic nerve surgery 14 days previously to initiate the regenerative response were dissociated and cultured in the presence of either control (L-15) medium alone, unfractionated CM at a 10% concentration, or the low molecular weight fraction of CM at a 10% concentration. In all cases, the response of RGCs was unaffected by the 'priming' lesion.

This was done to determine whether the neurite-promoting factors in CM would allow 'naive' retinal ganglion cells to grow to the same extent as 'primed' cells in which the regenerative process had been initiated in vivo. Four retinas from previously intact fish were pooled, as were 4 retinas from fish that had undergone bilateral optic nerve surgery 10 days previously. Like 'naive' retinal ganglion cells, 'primed' RGCs showed little spontaneous outgrowth in control media. In the presence of either total (unfractionated) CM or the low molecular weight fraction alone (<3 kDa), neurons from 'naive' and 'primed' retinas showed identical levels of neurite outgrowth.

Activity of Other Molecules on Dissociated Retinal Cultures.

Whether other molecules which have been reported to alter the growth characteristics of retinal explant cultures would be active in this system was then determined. Taurine, retinoic acid, and NGF have all been reported to influence neurite outgrowth from retinal explants.

Lima, et al. (1989) reported that taurine, in the presence of laminin, augments neurite outgrowth from retinal explants primed to regenerate in vivo, but has little effect on previously intact retina. Taurine also contributes to the differentiation of rod cells (Altschuler, et al. (1993) *Development*, 119:1317–1328). In this cell system, taurine, at concentrations between 1 μm and 10 mM, had no effect at all, nor did retinoic acid at concentrations between $10^{-9}$ and $10^{-4}$.

Retinoic acid (RA), a prominent factor in cell differentiation, has been found to enhance the expression of the intermediate filament proteins $ON_1$ (gefiltin) and $ON_2$ in goldfish retinal explants without affecting outgrowth per se (Hall, et al., 1990). In the present study, RA (between $10^{-9}$ to $10^{-4}$M) had no measurable effect.

Preliminary experiments found no effects of NGF on dissociated retinal neurons at 50 nM and weak stimulation at 500 nM; the results show an absence of NGF activity at 100 nM, 20 times the dosage that enhances axonal outgrowth in primed explant cultures (Turner, et al., 1982).

Although nerve growth factor (NGF) failed to elicit neurite outgrowth in these cultures, it may nevertheless contribute to optic nerve regeneration in an indirect fashion. NGF activity has been demonstrated in the goldfish brain (Benowitz & Greene, (1979) *Brain Res.*, 162:164–168), and the presence of an NGF-like molecule in optic nerve CM is supported by preliminary western blot studies showing that antibodies to mouse NGF cross-react with a protein of 12–13 kDa, the expected size of the β-NGF monomer. At low concentrations (i.e., 5 ng/ml), the β-subunit of mammalian NGF augments neurite outgrowth from goldfish retinal explants which had been primed to grow in vivo, while antibodies to NGF suppress outgrowth from primed retinal explants maintained in the presence of serum (Turner, et al., 1982). However, NGF has little effect on explants of unprimed retina (turner, et al., 1982) nor on the rate of axonal outgrowth in vivo (Yip & Grafstein, 1982). Thus, although NGF is likely to play a modulatory role in this system, it does not seem to induce axonal outgrowth directly. NGF may stimulate glial cells to release factors which in turn act upon neurons.

The relationship of the two factors to one another is not clearly understood at this time. AF-1 and AF-2 can each induce neurite outgrowth independently in these assays, and their effects do not appear to be synergistic. Nevertheless, it is possible that in vivo they function in a complementary fashion. It is also possible that AF-1 derives from degradation of AF-2. Since the cultures contain a variety of cell types, it remains possible that AF-1 and AF-2 may not act directly upon retinal ganglion cells, but rather upon another cell type as an intermediary. As observed by Schwartz & Agranoff (1981), RGCs are the dominant cell type in dissociated goldfish retinal cultures prepared as described above, and support cells are not abundant. Thus, rather than suppressing proliferation of support cells, cell density was systematically reduced to decrease the concentration of any secondary factors that might be released by another cell type while holding the concentration of CM constant. Since neurite outgrowth did not decline significantly over a 9-fold decrease in cell density, the RGCs would appear to be responding to CM directly. At a cell density of c. 3 cells/$mm^2$, however, outgrowth did show a significant decline. This could result from a decreased concentration of a trophic factor, released from another cell type in culture or from RGCs themselves, this is required to maintain the cells in a state in which they can respond to CM.

These findings lend further support to the specificity of AF-1 and AF-2 in inducing axonal outgrowth from RGCs.

Modifications and variations will be obvious to those skilled in the art from the foregoing detailed description and are intended to be encompassed by the following claims.

The publications cited above are specifically incorporated by reference herein.

We claim:

1. An isolated neurotrophic polypeptide of the type that:
   (a) is present in medium in which goldfish glial sheath cells have been cultured;
   (b) stimulates axonal outgrowth of naive goldfish retinal ganglion cells;
   (c) has a molecular weight of about 8–15 KDa;
   (d) does not bind to polylysine coated plates;
   (e) is inactivated by heating at 95° C. for 15 minutes;
   (f) is inactivated by trypsin or proteinase K; and
   (g) binds to a DEAE-anion exchange resin at pH 10 but not pH 8.4, and is eluted from the DEAE-anion exchange resin with 0.2M NaCl.

* * * * *